United States Patent [19]

Leeson

[11] Patent Number: 5,270,309
[45] Date of Patent: Dec. 14, 1993

[54] KYNURENIC ACID DERIVATIVES USEFUL IN THE TREATMENT OF NEURODEGENERATIVE DISORDERS

[75] Inventor: Paul Leeson, Cambridge, England

[73] Assignee: Merck Sharp & Dohme Limited, Hoddesdon, United Kingdom

[21] Appl. No.: 916,929

[22] Filed: Jul. 20, 1992

Related U.S. Application Data

[63] Continuation of Ser. No. 716,435, Jun. 17, 1991, abandoned, which is a continuation of Ser. No. 533,255, Jun. 4, 1990, abandoned, which is a continuation of Ser. No. 228,191, Aug. 4, 1988, abandoned.

[30] Foreign Application Priority Data

Aug. 12, 1987 [GB] United Kingdom ............... 8719102

[51] Int. Cl.$^5$ .................. A61K 31/535; A61K 31/47; C07D 401/12; C07D 413/12
[52] U.S. Cl. .................. 514/235.2; 514/312; 544/128; 546/153; 546/156; 564/305; 564/441; 564/442; 568/936; 568/939
[58] Field of Search ............... 546/153, 156; 544/128; 514/312, 235.2

[56] References Cited

U.S. PATENT DOCUMENTS

| | | | |
|---|---|---|---|
| 4,328,230 | 5/1982 | Brown et al. | 514/292 |
| 5,026,700 | 6/1991 | Harrison et al. | 544/128 |
| 5,028,707 | 7/1991 | Nichols et al. | 546/156 |

FOREIGN PATENT DOCUMENTS

| | | |
|---|---|---|
| 2554772 | 5/1975 | Fed. Rep. of Germany . |
| 1207771 | 3/1969 | United Kingdom . |
| 1334705 | 6/1970 | United Kingdom . |

OTHER PUBLICATIONS

Evans, et al., Br. J. Pharmac., vol. 91 (1987) pp. 531–537.
Mutschler Arzneimittelwirkungen 5th Edition (1986), pp. 555–566.
Perkins, et al., Chem. Abs. 99, No. 25 (Dec. 19, 1983) p. 139, 206826b.
Neumuller Rompps Chemie-Lexikon (8th Ed.) 3 p. 2296 (1983).
Daeniker, et al., Chem. Abs. 54, No. 538 (1960).
Heindel, et al., J. Med. Chem. II, pp. 1218–1221 (1968).

Primary Examiner—Emily Bernhardt
Attorney, Agent, or Firm—Robert J. North; Joseph F. DiPrima

[57] ABSTRACT

4-Oxo-1,4-dihydroquinoline compounds having a 2-acidic group or a group convertible thereto in vivo, and their pharmaceutically acceptable salts, are potent specific antagonists of N-methyl-D-aspartate (NMDA) receptors and are therefore useful in the treatment of neurodegenerative disorders. 4-Oxo-1,4-dihydroquinoline compounds having a 2-acidic group or a group convertible thereto in vivo, other than carboxy or $C_{1-6}$ alkoxycarbonyl, are novel compounds, as also are compounds of formula II

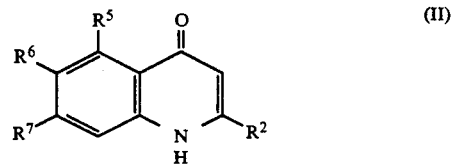

(II)

wherein $R^2$ represents carboxy or a group convertible thereto in vivo, $R^6$ is hydrogen and $R^5$ and $R^7$ represent $C_{1-6}$ alkyl or halogen, provided that $R^5$ and $R^7$ are not simultaneously chlorine or simultaneously bromine; a process for preparing the novel compounds is described, as also are pharmaceutical compositions containing the novel compounds.

5 Claims, No Drawings

KYNURENIC ACID DERIVATIVES USEFUL IN THE TREATMENT OF NEURODEGENERATIVE DISORDERS

BRIEF DESCRIPTION OF RELATED APPLICATIONS

The present invention is a continuation of U.S. Ser. No. 07/716,435, filed Jun. 17, 1991, now abandoned, being a continuation of U.S. Ser. No. 07/533,255, file on Jun. 4, 1990, now abandoned, being a continuation of U.S. Ser. No. 07/228,191, filed Aug. 4, 1988, now abandoned.

This invention relates to a class of kynurenic acid derivatives which are specific antagonists of N-methyl-D-aspartate (NMDA) receptors and are therefore useful in the treatment of neurodegenerative disorders, such as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Olivo-ponto-cerebellar atrophy, anoxia such as from drowning, spinal cord injury and poisoning by exogenous NMDA poisons. No satisfactory specific therapy for these neurodegenerative diseases is known. Of the competitive and non-competitive NMDA antagonists known to date, both types induce psychotomimetic side effects.

Certain derivatives of kynurenic acid (4-oxo-1,4-dihydroquinoline-2-carboxylic acid) are known as having therapeutic activity. British Patent No. 1,334,705 describes compounds of formula I:

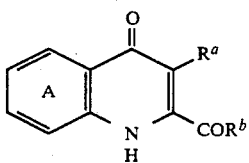

wherein $R^a$ is hydrogen, a methyl or ethyl radical, or a halogen atom, $R^b$ stands for a hydroxy or $C_{1-6}$ alkoxy radical, and the benzene ring A optionally bears a substituent selected from $C_{1-5}$ alkyl, $C_{1-5}$ alkoxy, benzyl, phenyl, benzyloxy, acetyl, halogen, trifluoromethyl, nitro and amino radicals, or wherein the said benzene ring A is optionally fused with an unsubstituted benzene ring, a methoxy-substituted benzene ring or a tetramethylene radical; for the treatment of allergic asthma in man.

U.S. Pat. No. 1,334,705 does not suggest that the kynurenic acid derivatives may possess any other utility apart from anti-allergic activity, and in particular provides no assistance in solving the problem of a treatment for neurodegenerative disorders.

Kynurenic acid (4-oxo-1,4-dihydroquinoline-2-carboxylic acid) is known to be a weak and non-selective antagonist of excitatory amino acid receptors (e.g. R. H. Evans et al., Br. J. Pharmac., 1987, 91, 531). It has now been found that certain derivatives of 4-oxo-1,4-dihydroquinoline-2-carboxylic acid are potent antagonists of the main subtypes of excitatory amino acid receptors, namely NMDA, kainate and quisqualate receptors. In particular, compounds possessing potent, selective NMDA antagonist properties have been found; these compounds have additionally been found to act as NMDA antagonists by selectively inhibiting the glycine modulation of NMDA receptors. Moreover, these compounds do not induce the undesirable psychotomimetic side-effects commonly induced by the NMDA antagonists known from the art. Some compounds are also potent kainate/quisqualate antagonists. Furthermore, certain novel derivatives of 4-oxo-1,4-dihydroquinoline having a different acidic moiety at the 2-position also have these utilities.

Accordingly this invention provides the use of a 4-oxo-1,4-dihydroquinoline having a 2-acidic group or a group convertible thereto in vivo, or a pharmaceutically acceptable salt thereof; for the preparation of a medicament useful for the prevention or treatment of neurodegenerative disorders.

The benzo moiety in the dihydroquinoline ring system may be substituted or unsubstituted. Suitable substituents include a hydrocarbon group or a functional substituent such as hydroxy, halogen, amino, carboxy, alkoxy, alkylthio, trifluoromethyl or cyano.

The acidic group at the 2-position of the dihydroquinoline nucleus may represent for example a carboxylic acid group, carboxyalkyl, or a group which is convertible to a carboxy or carboxyalkyl group; hydroxamic acid; tetrazolyl; or tetrazolylalkyl.

Specifically, the invention provides the use of a compound of formula II:

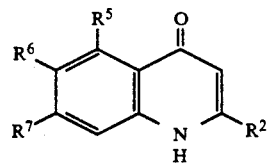

or a pharmaceutically acceptable salt thereof, wherein $R^2$ represents an acidic group, or a group which is convertible thereto in vivo, and $R^5$, $R^6$ and $R^7$ independently represent hydrogen, hydrocarbon, hydroxy, halogen, amino, carboxy, alkoxy, alkylthio, trifluoromethyl or cyano; for the preparation of a medicament useful for the prevention or treatment of neurodegenerative disorders.

The invention also provides a compound of formula II for use as an NMDA antagonist.

It will be appreciated that the 4-oxo compound of formula II will in general be in tautomeric equilibrium with the 4-hydroxy compound of formula IIA:

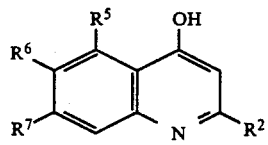

although under standard conditions the 4-oxo isomer of formula II will significantly predominate. It is to be understood that the tautomers of formula IIA, as well as all possible mixtures thereof with the isomers of formula II, are also included within the scope of the present invention.

The term 'hydrocarbon' includes groups having up to 18 carbon atoms, suitably up to 10 carbon atoms, conveniently up to 6 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, and aryl($C_{1-6}$)alkyl.

The alkyl group may be straight or branched chain and may contain, for example, up to 12 carbon atoms, suitably from 1 to 6 carbon atoms. In particular the group may be methyl, ethyl, n- or iso-propyl, or n-, sec-, iso- or tert-butyl.

The aliphatic hydrocarbon groups may optionally carry one or more substituents. Suitable substituents include, for example, halogen, hydroxy, $C_{1-6}$ alkoxy and trifluoromethyl groups.

When used herein the term 'aryl' includes phenyl and naphthyl optionally substituted with up to five, preferably up to three, groups suitably selected from halogen, $C_{1-6}$ alkyl, phenyl, $C_{1-6}$ alkoxy, halo($C_{1-6}$)alkyl, hydroxy, amino, nitro, carboxy, $C_{1-6}$ alkoxycarbonyl, $C_{1-6}$ alkoxycarbonyl($C_{1-6}$)alkyl, $C_{1-6}$ alkylcarbonyloxy, and $C_{1-6}$ alkylcarbonyl groups.

The term 'halogen' refers to fluorine, chlorine, bromine and iodine.

The acidic group $R^2$ may represent carboxy, carboxyalkyl, or a group convertible thereto in vivo such as an in vivo hydrolysable ester or amido group. Such groups may be represented by the moiety $-(CH_2)_nCOX$ wherein n is zero, 1 or 2, and X is OR or $NR^pR^q$, where R is hydrogen or an in vivo hydrolysable ester residue and $R^p$ and $R^q$ are independently hydrogen, hydrocarbon or in vivo hydrolysable amido residues.

Examples of suitable in vivo hydrolysable ester and amido groups for $R^2$ include those which break down readily in the human body to leave the parent acid or its salt. Suitable ester and amido groups $R^2$ of this type include those of part formulae (i)–(v):

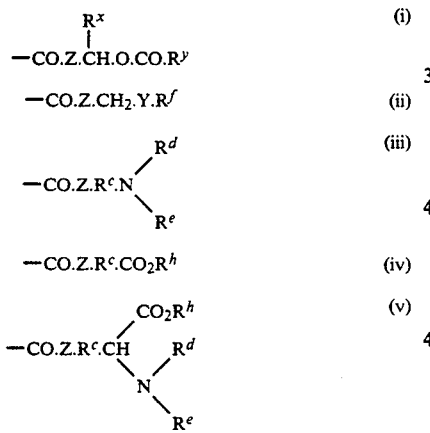

wherein Z is O or NH; $R^x$ is hydrogen, $C_{1-6}$ alkyl or phenyl; $R^y$ is $C_{1-6}$ alkyl, $C_{1-6}$ alkoxy or phenyl, any of which may be optionally substituted by amino or a group of the formula $-NR^dR^e$; or $R^x$ and $R^y$ together form a 1,2-phenylene group; $R^c$ represents $C_{1-6}$ alkylene optionally substituted with a $C_{1-6}$ alkyl group; $R^d$ and $R^e$ independently represent $C_{1-6}$ alkyl, aryl or aryl ($C_{1-6}$) alkyl, or $R^d$ and $R^e$ together with the intervening nitrogen atom represent a pyrrolidino, piperidino or morpholine group; Y represents oxygen or sulphur; $R^f$ represents $C_{1-6}$ alkyl, aryl or aryl ($C_{1-6}$) alkyl; and $R^h$ represents hydrogen or $C_{1-6}$ alkyl. Thus, suitable in vivo hydrolysable ester and amido residues include, for example, acyloxyalkyl groups such as acetoxymethyl, pivaloyloxymethyl, α-acetoxyethyl and α-pivaloyloxyethyl groups; alkoxycarbonyloxyalkyl groups such as ethoxycarbonyloxymethyl and α-ethoxycarbonyloxyethyl; dialkylaminoalkyl especially di-loweralkylaminoalkyl groups such as dimethylaminomethyl, dimethylaminoethyl, diethylaminomethyl or diethylaminoethyl; and heterocyclylalkyl groups such as pyrrolidinylethyl or morpholinoethyl.

Alternatively, the acidic group $R^2$ may represent any other group which can provide an anion, for example a hydroxamic acid derivative of formula $-CONR^pOH$ or $-CONH.OR^p$ where $R^p$ is defined above; or tetrazolyl or tetrazolYl($C_{1-3}$)alkyl; or a derivative of any of these groups which is hydrolysable thereto in vivo.

One subclass of compounds useful in this invention is represented by the formula IIIA:

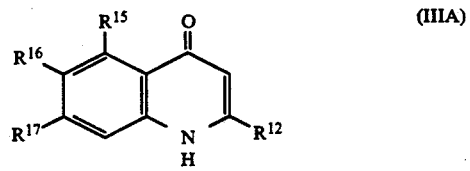

wherein $R^{12}$ is carboxy, $C_{1-6}$ alkoxycarbonyl or $CONHR^z$ where $R^z$ represents hydrogen, hydroxy or $C_{1-6}$ alkoxy; and $R^{15}$, $R^{16}$ and $R^{17}$ independently represent halogen, trifluoromethyl, $C_{1-6}$ alkyl, $C_{2-6}$ alkenyl, hydroxy or cyano.

A further subclass of compounds useful in this invention is represented by the formula IIIB:

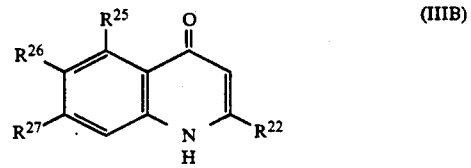

wherein $R^{22}$ is carboxy, $CONHR^k$, in which $R^k$ represents hydroxy or aryl($C_{1-6}$)alkoxy, or $CO.Z.R^c.NR^dR^e$, in which Z, $R^c$, $R^d$ and $R^e$ are as hereinbefore defined; and $R^{25}$, $R^{26}$ and $R^{27}$ independently represent halogen, trifluoromethyl, $C_{1-6}$ alkyl, $C_{2-6}$ alkenyl, $C_{1-6}$ alkoxy, $C_{1-6}$ alkylthio or nitro.

Suitable pharmaceutically acceptable salts of the compounds of this invention include metal salts, such as for example aluminium, alkali metal salts such as sodium or potassium, alkaline earth metal salts such as calcium or magnesium and ammonium or substituted ammonium salts, for example those with lower alkylamines such as triethylamine.

Compounds of formula II substituted at the 2 and 5 positions, at the 2 and 7 positions, and also at the 2, 5 and 7 positions, selectively antagonise the NMDA receptor. Preferred compounds include:
5-ethyl-4-oxo-1,4-dihydroquinoline-2-carboxylic acid;
5-iodo-4-oxo-1,4-dihydroquinoline-2-carboxylic acid;
5-bromo-7-methyl-4-oxo-1,4-dihydroquinoline-2-carboxylic acid;
7-bromo-5-methyl-4-oxo-1,4-dihydroquinoline-2-carboxylic acid;
7-bromo-5-ethyl-4-oxo-1,4-dihydroquinoline-2-carboxylic acid;
5,7-dimethyl-4-oxo-1,4-dihydroquinoline-2-carboxylic acid;
5,7-dichloro-4-oxo-1,4-dihydroquinoline-2-hydroxamic acid;
5,7-dichloro-4-oxo-1,4-dihydroquinoline-2-carboxylic acid;

5,7-dibromo-4-oxo-1,4-dihydroquinoline-2-carboxylic acid;
7-chloro-5-iodo-4-oxo-1,4-dihydroquinoline-2-carboxylic acid;
7-chloro-5-ethyl-4-oxo-1,4-dihydroquinoline-2-carboxylic acid;
5-iodo-7-methyl-4-oxo-1,4-dihydroquinoline-2-carboxylic acid;
5,7-dichloro-2-(2-dimethylaminoethyl)carbamoyl-4-oxo-1,4-dihydroquinoline;
2-(diethylamino)ethyl 5,7-dichloro-4-oxo-1,4-dihydroquinoline-2-carboxylate;
2-(1-pyrrolidinyl)ethyl 5,7-dichloro-4-oxo-1,4-dihydroquinoline-2-carboxylate;
2-(4-morpholinyl)ethyl 5,7-dichloro-4-oxo-1,4-dihydroquinoline-2-carboxylate; and
2-(diethylamino)ethyl 7-chloro-5-iodo-4-oxo-dihydroquinoline-2-carboxylate.

Compounds of formula II substituted at the 2, 5, 6 and 7 positions potently antagonise the NMDA, kainate and quisqualate receptors, for example: 5,6,7-trichloro-4-oxo-1,4-dihydroquinoline-2-carboxylic acid.

Compounds of formula II substituted at the 2 and 6 positions have selective antagonist activity at kainate and quisqualate receptors, for example the following compounds:
6-chloro-4-oxo-1,4-dihydroquinoline-2-carboxylic acid;
6-bromo-4-oxo-1,4-dihydroquinoline-2-carboxylic acid; and
6-methylthio-4-oxo-1,4-dihydroquinoline-2-carboxylic acid.

Within the formula II above, certain compounds are novel and form a further aspect of this invention.

Accordingly the invention also provides a 4-oxo-1,4-dihydroquinoline having a 2-acidic group or a group convertible thereto in vivo, other than carboxy or $C_{1-6}$ alkoxycarbonyl; or a pharmaceutically acceptable salt thereof.

A further group of novel compounds are compounds of formula II wherein $R^2$ represents carboxy or a group convertible thereto in vivo, $R^6$ is hydrogen and $R^5$ and $R^7$ represent $C_{1-6}$ alkyl or halogen, provided that $R^5$ and $R^7$ are not simultaneously chlorine or simultaneously bromine.

Preferably $R^5$ and $R^7$ are different from each other. Examples of such compounds are:
7-bromo-5-methyl-4-oxo-1,4-dihydroquinoline-2-carboxylic acid;
5-bromo-7-methyl-4-oxo-1,4-dihydroquinoline-2-carboxylic acid;
7-bromo-5-ethyl-4-oxo-1,4-dihydroquinoline-2-carboxylic acid;
5-bromo-7-ethyl-4-oxo-1,4-dihydroquinoline-2-carboxylic acid;
7-bromo-5-iodo-4-oxo-1,4-dihydroquinoline-2-carboxylic acid;
7-chloro-5-iodo-4-oxo-1,4-dihydroquinoline-2-carboxylic acid;
5-chloro-7-iodo-4-oxo-1,4-dihydroquinoline-2-carboxylic acid;
5-iodo-7-methyl-4-oxo-1,4-dihydroquinoline-2-carboxylic acid;
7-iodo-5-methyl-4-oxo-1,4-dihydroquinoline-2-carboxylic acid; 5-ethyl-7-methyl-4-oxo-1,4-dihydroquinoline-2-carboxylic acid;
7-chloro-5-ethyl-4-oxo-1,4-dihydroquinoline-2-carboxylic acid;
5-chloro-7-ethyl-4-oxo-1,4-dihydroquinoline-2-carboxylic acid;
5-chloro-7-methyl-4-oxo-1,4-dihydroquinoline-2-carboxylic acid;
5-methyl-7-chloro-4-oxo-1,4-dihydroquinoline-2-carboxylic acid;
7-bromo-5-chloro-4-oxo-1,4-dihydroquinoline-2-carboxylic acid;
7-chloro-5-bromo-4-oxo-1,4-dihydroquinoline-2-carboxylic acid;
5,7-dimethyl-4-oxo-1,4-dihydroquinoline-2-carboxylic acid;
2-(diethylamino)ethyl 5,7-dichloro-4-oxo-1,4-dihydroquinoline-2-carboxylate;
5,7-dichloro-2-(2-dimethylaminoethyl)carbamoyl-4-oxo-1,4-dihydroquinoline;
2-(1-pyrrolidinyl)ethyl 5,7-dichloro-4-oxo-1,4-dihydroquinoline-2-carboxylate;
2-(4-morpholinyl)ethyl 5,7-dichloro-4-oxo-1,4-dihydroquinoline-2-carboxylate;
5,7-dichloro-2-[2-(4-morpholinyl)ethyl]carbamoyl-4-oxo-1,4-dihydroquinoline;
5,7-dichloro-2-[2-(1-pyrrolidinyl)ethyl]carbamoyl-4-oxo-1,4-dihydroquinoline;
2-(diisopropylamino)ethyl 5,7-dichloro-4-oxo-1,4-dihydroquinoline-2-carboxylate;
3-(dimethylamino)propyl 5,7-dichloro-4-oxo-1,4-dihydroquinoline-2-carboxylate;
(2-dimethylamino--methyl)ethyl 5,7-dichloro-4-oxo-1,4-dihydroquinoline-2-carboxylate;
2-(diethylamino)ethyl 7-chloro-5-iodo-4-oxo-1,4-dihydroquinoline-2-carboxylate; and
2-(diethylamino)ethyl 7-bromo-5-ethyl-4-oxo-1,4-dihydroquinoline-2-carboxylate.

In addition the following compounds have a 2-carboxy substituent, but are not specifically disclosed in the prior art. These compounds and their methyl and ethyl esters therefore are also novel compounds of this invention:
5-fluoro-4-oxo-1,4-dihydroquinoline-2-carboxylic acid;
5-trifluoromethyl-4-oxo-1,4-dihydroquinoline-2-carboxylic acid;
5-ethyl-4-oxo-1,4-dihydroquinoline-2-carboxylic acid;
5-iodo-4-oxo-1,4-dihydroquinoline-2-carboxylic acid;
5-n-propyl-4-oxo-1,4-dihydroquinoline-2-carboxylic acid;
5-n-butyl-4-oxo-1,4-dihydroquinoline-2-carboxylic acid;
4-oxo-5-ethenyl-1,4-dihydroquinoline-2-carboxylic acid;
5,6,7-trichloro-4-oxo-1,4-dihydroquinoline-2-carboxylic acid;
4-oxo-7-ethenyl-1,4-dihydroquinoline-2-carboxylic acid; and
6-methylthio-4.-oxo-1,4-dihydroquinoline-2-carboxylic acid.

The following compounds likewise possess a 2-carboxy substituent and are not disclosed in the prior art. Thus, these compounds and their methyl and ethyl esters are further novel compounds of this invention:
5-isopropyl-4-oxo-1,4-dihydroquinoline-2-carboxylic acid;
7-n-propyl-4-oxo-1,4-dihydroquinoline-2-carboxylic acid;
7-n-butyl-4-oxo-1,4-dihydroquinoline-2-carboxylic acid;
7-isopropyl-4-oxo-1,4-dihydroquinoline-2-carboxylic acid;

5-hydroxy-4-oxo-1,4-dihydroquinoline-2-carboxylic acid;

5-cyano-4-oxo-1,4-dihydroquinoline-2-carboxylic acid; and 6-trifluoromethyl-4-oxo-1,4-dihydroquinoline-2-carboxylic acid.

The invention also provides pharmaceutical compositions comprising the compounds of this invention. Preferably these compositions are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil and peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone, and gelatine.

In the treatment of neurodegeneration, a suitable dosage level is about 0.01 to 250 mg/kg, preferably about 0.05 to 100 mg/kg and especially about 0.05 to 5 mg/kg/day. The compounds may be administered on a regimen of 1 to 4 times per day.

The compounds of formula II above, including the novel compounds of this invention, may be prepared by a process which comprises the cyclisation of a compound of formula IV:

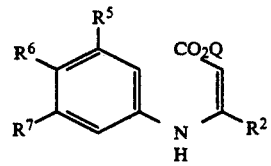

wherein $R^2$, $R^5$, $R^6$ and $R^7$ are as defined with respect to formula II, in which any reactive groups may be protected, and $CO_2Q$ represents an ester moiety; optionally converting one group $R^2$ to another group $R^2$; and thereafter if necessary removing the protecting groups. Preferably Q represents $C_{1-6}$ alkyl.

The cyclisation reaction may be performed at elevated temperatures, for example at a temperature of 80°–100° C. in polyphosphoric acid; or at 230°–260° C., for example about 250° C., in diphenyl ether or α-chloronaphthalene.

The protecting groups employed, and the methods of removal thereof, may be those which are conventional in the art.

In a variant of the above process, it may be necessary or convenient to protect the oxygen substituent in the 4 position prior to conversion of one group $R^2$ to another group $R^2$. Thus, the 4-substituent may, for example, conveniently be protected as the benzyl derivative, as shown in the following scheme:

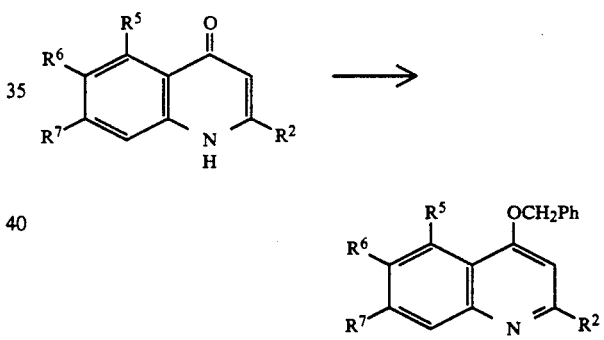

This conversion can be brought about by reacting the appropriate 4-oxo compound with a benzyl halide (e.g. benzyl bromide) in the presence of a mild base such as, for example, sodium carbonate. Subsequent removal of the benzyl protecting group can be effected, when required, by standard techniques such as acid-catalysed hydrolysis (using, for example, a mixture of hydrobromic acid and acetic acid) or catalytic hydrogenation.

The intermediate compounds of formula IV may be prepared by reaction of an aniline of formula V:

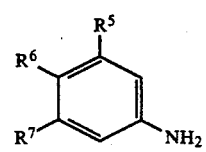

with a compound of formula VI or VII:

-continued

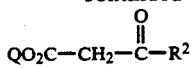
VII

The anilines of formula V may be prepared by the methods described in the accompanying Examples.

The effects of compounds of the invention on responses to the agonists NMDA, kainate and quisqualate were assessed using the rat cortical slice preparation as described by Wong et al., *Proc. Natl. Acad. Sci. U.S.A.*, 1986, 83, 7104. The apparent equilibrium constants ($K_b$) were calculated from the righthand shift in the agonist concentration-response curve.

Using the above techniques, the following compounds were found to have NMDA antagonist activity at concentrations ($K_b$) below 100 µM:
5-ethyl-4-oxo-1,4-dihydroquinoline-2-carboxylic acid;
7-bromo-5-methyl-4-oxo-1,4-dihydroquinoline-2-carboxylic acid;
5-bromo-7-methyl-4-oxo-1,4-dihydroquinoline-2-carboxylic acid;
7-bromo-5-ethyl-4-oxo-1,4-dihydroquinoline-2-carboxylic acid;
5-bromo-7-ethyl-4-oxo-1,4-dihydroquinoline-2-carboxylic acid;
5-iodo-4-oxo-1,4-dihydroquinoline-2-carboxylic acid;
5-fluoro-4-oxo-1,4-dihydroquinoline-2-carboxylic acid;
5-trifluoromethyl-4-oxo-1,4-dihydroquinoline-2-carboxylic acid;
5,7-dimethyl-4-oxo-1,4-dihydroquinoline-2-carboxylic acid; 5,7-dichloro-4-oxo-1,4-dihydroquinoline-2-hydroxamic acid; 5,7-dichloro-4-oxo-1,4-dihydroquinoline-2-(O-benzyl)hydroxamic acid;
7-chloro-5-ethyl-4-oxo-1,4-dihydroquinoline-2-carboxylic acid;
5-chloro-7-ethyl-4-oxo-1,4-dihydroquinoline-2-carboxylic acid;.
5-chloro-7-iodo-4-oxo-1,4-dihydroquinoline-2-carboxylic acid;
7-chloro-5-iodo-4-oxo-1,4-dihydroquinoline-2-carboxylic acid;
5-iodo-7-methyl-4-oxo-1,4-dihydroquinoline-2-carboxylic acid;
7-iodo-5-methyl-4-oxo-1,4-dihydroquinoline-2-carboxylic acid;
5-chloro-4-oxo-1,4-dihydroquinoline-2-carboxylic acid;
5-bromo-4-oxo-1,4-dihydroquinoline-2-carboxylic acid;
5-methyl-4-oxo-1,4-dihydroquinoline-2-carboxylic acid;
7-fluoro-4-oxo-1,4-dihydroquinoline-2-carboxylic acid;
7-chloro-4-oxo-1,4-dihydroquinoline-2-carboxylic acid;
7-bromo-4-oxo-1,4-dihydroquinoline-2-carboxylic acid;
7-iodo-4-oxo-1,4-dihydroquinoline-2-carboxylic acid;
7-nitro-4-oxo-1,4-dihydroquinoline-2-carboxylic acid;
5,7-dichloro-4-oxo-1,4-dihydroquinoline-2-carboxylic acid;
5,7-dibromo-4-oxo-1,4-dihydroquinoline-2-carboxylic acid;
6-fluoro-4-oxo-1,4-dihydroquinoline-2-carboxylic acid; and
7-methyl-4-oxo-1,4-dihydroquinoline-2-carboxylic acid.

Similarly, the following compounds were found to have quisqualate antagonist activity at concentrations ($K_b$) below 100 µm:
5-fluoro-4-oxo-1,4-dihydroquinoline-2-carboxylic acid;
5,6,7-trichloro-4-oxo-1,4-dihydroquinoline-2-carboxylic acid;
6-methylthio-4-oxo-1,4-dihydroquinoline-2-carboxylic acid;
5-chloro-4-oxo-1,4-dihydroquinoline-2-carboxylic acid;
7-chloro-4-oxo-1,4-dihydroquinoline-2-carboxylic acid;
6-methyl-4-oxo-1,4-dihydroquinoline-2-carboxylic acid;
6-fluoro-4-oxo-1,4-dihydroquinoline-2-carboxylic acid;
6-chloro-4-oxo-1,4-dihydroquinoline-2-carboxylic acid;
6-bromo-4-oxo-1,4-dihydroquinoline-2-carboxylic acid;
6-iodo-4-oxo-1,4-dihydroquinoline-2-carboxylic acid;
6-methoxy-4-oxo-1,4-dihydroquinoline-2-carboxylic acid; and
6-nitro-4-oxo-1,4-dihydroquinoline-2-carboxylic acid.

The following compounds were found to have kainate antagonist activity at concentrations ($K_b$) below 100 µM:
5-fluoro-4-oxo-1,4-dihydroquinoline-2-carboxylic acid;
5,6,7-trichloro-4-oxo-1,4-dihydroquinoline-2-carboxylic acid;
6-methylthio-4-oxo-1,4-dihydroquinoline-2-carboxylic acid;
7-chloro-4-oxo-1,4-dihydroquinoline-2-carboxylic acid;
6-methyl-4-oxo-1,4-dihydroquinoline-2-carboxylic acid;
6-fluoro-4-oxo-1,4-dihydroquinoline-2-carboxylic acid;
6-chloro-4-oxo-1,4-dihydroquinoline-2-carboxylic acid;
6-iodo-4-oxo-1,4-dihydroquinoline-2-carboxylic acid;
6-methoxy-4-oxo-1,4-dihydroquinoline-2-carboxylic acid;
6-nitro-4-oxo-1,4-dihydroquinoline-2-carboxylic acid; and
7-methyl-4-oxo-1,4-dihydroquinoline-2-carboxylic acid.

The invention is illustrated by the following Examples:

EXAMPLE 1

5-Propyl-4-oxo-1,4-dihydroquinoline-2-carboxylic acid a) To a suspension of ethyltriphenylphosphonium bromide (22 g) in tetrahydrofuran (150 ml) at −78° C. was added dropwise a solution of n-butyllithium in hexane (59.3 mmol). The mixture was left to warm to room temperature over 30 minutes, then cooled to −78° C. and a solution of 3-nitrobenzaldehyde (7.5 g) in tetrahydrofuran (50 ml) was added dropwise. The reaction was left to warm to room temperature over 1 hour, poured into 2M hydrochloric acid (100 ml) and ethyl acetate (100 ml). The separated aqueous layer was extracted with ethyl acetate, the organic layers were combined and washed with water, saturated sodium bicarbonate (2×50 ml), brine (2×50 ml) and dried over magnesium sulphate. The solvent was removed under reduced pressure and the crude product purified by column chromatography to give 3-(2-propenyl)nitrobenzene (5.72 g). δ(60 MHz, CDCl$_3$) 1.9 (3H,2d, CH$_3$), 5.9 (1H, m, =CH—CH$_3$), 6.3 (1H, 2d, AR—CH) and 7.3–8.1 (4H, m, ArH). To a solution of the above 3-(2-propenyl)-nitrobenzene (5.7 g) in ethyl acetate (20 ml) was added 10% palladium on carbon (0.57 g). This mixture was hydrogenated at 50 psi for 2 hours at room temperature, filtered through Hyflo and solvent evaporated to yield the crude product which was purified by column chromatography to give 3-propylaniline (4.7 g), δ (60 MHz, CDCl$_3$) 0.9 (3H, t, CH$_3$), 1.5 (2H, m, CH$_2$CH$_3$), 2.4 (2H, t, CH$_2$CH$_2$CH$_3$), 3.4 (2H, bs, NH$_2$) and 6.1 to 7.0 (4H, m, ArH).

b) To a solution of 3-propylaniline (4.7 g) in methanol (100 ml) was added diethylacetylene dicarboxylate (5.5 ml) at room temperature. The mixture was refluxed for 10 hours and left to cool to room temperature. The methanol was removed under reduced pressure to give the intermediate enamine, which was added to diphenylether (100 ml) at 250° C. After 15 minutes the mixture was left to cool to room temperature. Hexane (500 ml) was added and the precipitate filtered off to give a crude mixture of two products which were separated using column chromatography to yield ethyl 5-propyl-4-oxo-1,4-dihydroquinoline-2-carboxylate (0.62 g), mp 177°–178° C. δ (360 MHz, DMSO-d6) 0.91 (3H, t, is $CH_2CH_2CH_3$), 1.36 (3H, t, $CO_2CH_2CH_3$), 1.52 (2H, dt, $CH_2CH_2CH_3$), 3.22 (2H, t, $CH_2CH_2CH_3$). 4.41 (2H, g, $CO_2CH_2$), 6.55 (1H, s, 3-H), 7.05 (1H, dd, 6-H), 7.52 (1H, dd, 7-H), 7.78 (1H, dd, 8-H) and 11.7 (1H, bs), and ethyl 7-propyl-4-oxo-1,4-dihydroquinoline-2-carboxylate (1.3 g), mp 153°–154° C. (360 MHz, DMSO-d6) 0.92 (3H, t, $CH_2CH_2CH_3$), 1.37 (3H, t, $CO_2CH_2CH_3$), 1.64 (2H, dt, $CH_2CH_2CH_3$), 2.67 (2H, t, $CH_2CH_2CH_3$), 4.40 (2H, q, $CO_2CH_2$), 6.63 (1H, s, 3-H), 7.23 (1H, dd, 6-H) 7.74 (1H, s, 8-H), 8.00 (1H, d, 5-H) and 11.88 (1H, bs).

c) To ethyl 5-propyl-4-oxo-1,4-dihydroquinoline-2-carboxylate (0.5 g) was added sodium hydroxide (0.309 g) in water (100 ml) and ethanol (40 ml). This mixture was heated to 100° C. for 1 hour. Hydrochloric acid (1M) was added until pH2 and the resulting precipitate was filtered off, washed with water (10 ml) ethanol (10 ml), diethylether (5 ml) and dried to give 5-propyl-4-oxo-1,4-dihydroquinoline-5 2-carboxylic acid (0.424 g), mp>240° C., δ (360 MHz, DMSO-d6) 0.91 (3H, t, $CH_3$), 1.53 (2H, dt, $CH_2CH_3$). 3.22 (2H, t, $CH_2CH_2$) 6.53 (1H, s, 3-H). 7.03 (1H, dd, 6-H), 7.51 (1H, dd, 7-H) and 7.80 (1H, dd, 8H), (Found: C. 67.47; H, 5.65; N, 6.20%; $C_{13}H_{13}NO_3$ requires C, 67.52: H, 5.68.; N, 6.06%).

EXAMPLE 2

7-Propyl-4-oxo-1,4-dihydroquinoline-2-carboxylic acid

Treatment of ethyl 7-propyl-4-oxo-1,4-dihydroquinoline-2 carboxylate (0.5 g, Example 1b) with sodium hydroxide (0.309 g), as described in Example 1c, gave 7-propyl-4-oxo-1,4-dihydroquinoline-2-carboxylic acid (0.4 g), mp>240° C. δ (360 MHz, DMSO-d6) 0.92 (3H, t, $CH_3$), 1.64 (2H, dt, $CH_2CH_3$) 2.66 (2H, t, $CH_2CH_2CH_3$), 6.59 (1H, s, 3-H), 7.20 (1H, dd, 6-H), 7.74 (1H, s, 8-H) and 7.98 (1H, d, 5-H), (Found: C, 64.66; H, 6.08; N, 6.22%. $C_{13}H_{13}NO_3$. $0.6H_2O$ requires C, 64.51; H, 5.91; N, 5.79%).

EXAMPLE 3

5-Ethyl-4-oxo-1,4-dihydroquinoline-2-carboxylic acid a) Using the method described in Example 1b with 3-ethylaniline (22.4 ml) and dimethylacetylene dicarboxylate (20.9 ml) as reagents gave, after chromatography on a 5 g portion of crude product, methyl 5-ethyl-4-oxo-1,4-dihydroquinoline-2-carboxylate (0.83g), m.p. 210°–211° C., a (360 MHz, DMSO-d6) 1.15 (3H, t, $CH_3$), 3.27 (2H, q, $CH_2$), 3.96 (3H, s, $CH_3O$), 6.56 (1H, s, 3-H), 7.07 (1H, d, 6-H), 7.54 (1H, t, 7-H) and 7.80 (1H, d, 8-H), (Found: C, 67.42; H, 5.44; N, 5.96%. $C_{13}H_{13}NO_3$ requires C, 67.52; H, 5.67; N, 6.06%) and methyl 7-ethyl-4-oxo-dihydroquinoline-2-carboxylate (1.04 g), m.p. 198°–199° C., δ (360 MHz, DMSO-d6) 1.24 (3H, t, $CH_3$), 2.73 (2H, q, $CH_2$), 3.96 (3H, s, $CH_3O$), 6.62 (1H, s, 3-H), 7.24 (1H, d, 6-H), 7.76 (1H, s, H-8). 7.99 (1H, d, H-5) and 11.81 (1H, s, NH), (Found: C, 67.33; H, 5.41; N, 6.23%, $C_{13}H_{13}NO_3$ requires C, 67.52; H, 5.67; N, 6.06%).

b) Treatment of methyl 5-ethyl-4-oxo-1,4-dihydroquinoline-2-carboxylate (0.61 g) with sodium hydroxide (0.42 g), as described in Example 1c, gave 5-ethyl-4-oxo-1,4-dihydroquinoline-2-carboxylic acid (0.34 g), m.p. 272°–273° C., δ (360 MHz, NAOD) 1.22 (3H, t, $CH_3$), 3.41 (2H, q, $CH_2$), 6.65 (1H, s. 3-H), 7.18 (1H, d, 6-H), 7.54 (1H, t, 7-H), 7.68 (1H, d, 8-H), 11.94 (1H, s, NH), (Found: C, 65.97; H, 4.86; N, 6.72%, $C_{12}H_{11}NO_3$ requires C, 66.35; H, 5.10; N, 6.45%).

EXAMPLE 4

7-Ethyl-4-oxo-1,4-dihydroquinoline-2-carboxylic acid

Treatment of methyl 7-ethyl-4-oxo-1,4-dihydroquinoline-2-carboxylate (0.8 g, Example 3a) with sodium hydroxide (0.58 g) as described in Example 1c, gave 7-ethyl-4-oxo-1,4-dihydroquinoline-2-carboxylic acid (0.66g), m.p. 271° C., δ (360 MHz, NaOD) 1.30 (3H, t, $CH_3$), 2.81 (2H, q, $CH_2$), 6.66 (1H, s, 3-H), 7.36 (1H, d, 6-H), 7.66 (1H, s, 8-H) and 8.11 (1H, d, 5-H), (Found: C, 66.46: H, 5.01; N, 6.59%, $C_{12}H_{11}NO_3$ requires C, 66.35; H, 5.10: N, 6.45%).

EXAMPLE 5

5-Butyl-4-oxo-1,4-dihydroquinoline-2-carboxylic acid a) Treatment of 3-nitrobenzaldehyde (8.2 g) with propyltriphenyl phosphonium bromide (25 g) and n-butyllithium in hexane (64.9 mmol), as described in Example 1a, gave 3-(2-butenyl)nitrobenzene (9.3 g), δ (360 MHz, CDCl3) 1.1 (3H, t, $CH_3$), 2.4 (2H, m, $CH_2CH_3$). 5.8 (1H, m, =CH—$CH_2$), 6.3 (1H, m, $CH$=$CH_2$), 7.2 to 8.0 (4H, m, ArH). Treatment of the above 3-(2-butenyl)nitrobenzene (9.3 g) with hydrogen and palladium on carbon (10%, 0.93 g) as described in Example 1a, gave 3-butylaniline (7.0 g), δ (60 MHz, $CDCl_2$) 0.9 (3H, t, $CH_3$), 1.4 (4H, m, $CH_2CH_2CH_3$), 2.5 (2H, t, $ARCH_2$), 3.4 (2H, bs, $NH_2$) and 6.2 to 7.0 (4H, m, ArH).

b) Treatment of 3-butylaniline (7 g) with diethylacetylene dicarboxylate (7.5 ml), as described in Example 1b, gave ethyl 5-butyl-4-oxo-1,4-dihydroquinoline-2-carboxylate (0.62 g) mp 132°–133° C., δ (360 MHz, DMSO-d6) 0.89 (3H, t, $CH_2CH_2CH_3$), 1.36 (5H, m, $CO_2CH_2CH_3$ and $CH_2CH_2CH_3$), 1.47 (2H, m, $CH_2CH_2CH_2$), 3.25 (2H, t, $CH_2CH_2CH_3$), 4.41 (2H, q, $CO_2CH_2$), 6.55 (1H, s, 3-H), 7.04 (1H, d, 8-H), 7.52 (1H, t, 7-H) 7.80 (1H, d, 6-H) and 11.75 (1H, bs, NH) and ethyl 7-butyl-4-oxo-1,4-dihydroquinoline-2-carboxylate (1.78 g), mp 124°–126° C., δ (360 MHz, DMSO-d6) 0.91 (3H, t, $CH_2CH_2CH_3$), 1.36 (5H, m, $CO_2CH_2CH_3$ and $CH_2CH_2CH_3$), 1.61 (2H, m, $CH_2CH_2CH_2$), 2.70 (2H, t, $CH_2CH_2CH_2$), 4.40 (2H, q, $CO_2CH_2$), 6.62 (1H, s, 3-H), 7.21 (1H, d, 6-H), 7.75 (1H, s, 8-H), 7.98 (1H, d, 5-H) and 11.87 (1H, bs, NH).

c) Treatment of ethyl 5-butyl-4-oxo-1,4-dihydroquinoline-2-carboxylate (0.5 g) with sodium hydroxide (0.293 g), as described in Example 1c, gave 5-butyl-4-oxo-1,4-dihydroquinoline-2-carboxylic acid (0.4 g), mp 269°–270° C., δ (360 MHz, DMSO-d6) 0.89 (3H, t, $CH_3$), 1.53 (2H, m, $CH_2CH_3$), 1.49 (2H, m, $CH_2CH_2CH_2$), 3.25 (2H, t, $CH_2CH_2CH_2$), 6.53 (1H, s, 3-H), 7.03 (1H, dd, 6-H), 7.50 (1H, t, 7-H) and 7.78 (1H, dd, 8-H), (Found: C, 67.55; H, 6.60: N, 5.88%, $C_{14}H_{15}NO_3$. $0.2H_2O$ requires C, 67.56; H, 6.24, N, 5.62%).

EXAMPLE 6

7-Butyl-4-oxo-1,4-dihydroquinoline-2-carboxylic acid

Treatment of ethyl 7-butyl-4-oxo-1,4-dihydroquinoline-2-carboxylate (0.5 g, Example 5b) with sodium hydroxide (0.326 g), as described in Example 1c, gave 7-butyl-4-oxo-1,4-dihydroquinoline-2-carboxylic acid (0.3 g), mp 247°-250° C. (decomp), δ (360 MHz, DMSO-d6) 0.91 (3H, t, $CH_3$), 1.32 (2H, m, $CH_2CH_3$), 1.60 (2H, m, $CH_2CH_2CH_2$), 2.69 (2H, t, $CH_2CH_2CH_2CH_3$), 6.60 (1H, s, 3-H), 7.20 (1H dd, 6-H), 7.75 (1H, s, 8-H) and 7.98 (1H, d. 5-H), (Found: C, 66.44; H, 6.68; N, 5.62%. $C_{14}H_{15}NO_3$. $0.5H_2O$ requires C, 66.13; H, 6.34; N, 5.51%).

EXAMPLE 7

5-(1-Methylethyl)-4-oxo-1,4-dihydroquinoline-2-carboxylic acid a) Treatment of 3-nitroacetophenone (10 g) with methyltriphenyl phosphonium bromide (28 g) and n-butyllithium in hexane (78.4 mmol), as described in Example 1a, gave 3-(1-methylethenyl)nitrobenzene (9.5 g), δ (60 MHz, $CDCl_3$) 2.1 (3H, s, $CH_3$), 5.2 and 5.5 (2H, 2s, $CH_2$), 7.2 to 8.2 (4H, m, ArH). Treatment of the above 3-(1-methylethenyl)nitrobenzene (9.5 g) with hydrogen and palladium on carbon (10%, 1.9 g) as described in Example 1a, gave 3-(1-methylethyl)aniline (6.15 g), δ (60 MHz, $CDCl_3$) 1.1 (6H, d, $(CH_3)_2$), 2.6 (1H, m, CH) 3.4 (2H, bs, $NH_2$) and 6.1 to 7.0 (4H, m, ArH).

b) Treatment of 3-(1-methylethyl)aniline (6.0 g) with diethylacetylenedicarboxylate (7.1 ml), as described in Example 1b, gave ethyl 5-(1-methylethyl)-4-oxo-1,4-dihydroquinoline-2-carboxylate (0.23 g), mp 176°-178° C., δ (360 MHz, DMSO-d6) 1.19 (6H, d, $(CH_3)_2$), 1.36 (3H, t, $CO_2CH_2CH_3$), 4.41 (2H, q, $CO_2CH_2$), 4.84 (1H, m, $CH(CH_3)_2$), 6.56 (1H, S, 3-H). 7.28 (1H, d, 6-H), 7.58 (1H, t, 7-H), 7.79 (1H, d, 8-H) and 11.80 (1H, bs, NH), and ethyl 7-(1-methylethyl)-4-oxo-1,4-dihydroquinoline-2-carboxylate (1.17 g) mp 186°-188° C., (360 MHz, DMSO-d6) 1.25 (6H, d, $(CH_3)_2$),1.35 (3H, t, $CH_2CH_3$), 3.00 (1H, m, $CH(CH_3)_2$), 4.42 (2H, q, $CH_2$), 6.63 (1H, S, 3-H), 7.29 (1H, d, 6-H), 7.80 (1H, s, 8-H), 8.00 (1H, d, 5-H) and 11.86 (1H, bs, NH).

c) Treatment of ethyl S-(1-methylethyl)-4-oxo-1,4-dihydroquinoline-2-carboxylate (0.26 g) with sodium hydroxide (0.16 g), as described in Example 1c, gave 5-(1-methylethyl)-4-oxo-1,4-dihydroquinoline-2-carboxylic acid (0.118 g), mp>250° C. δ (360 MHz, DMSO-d6) 1.19 (6H, d, $(CH_3)_2$), 4.86 (1H, m, CH), 6.53 (1H, s, 3-H), 7.26 (1H, d, 6-H), 7.56 (1H, t, 7-H), 7.79 (1H, d, 8-H) and 11.75 (1H, bs, NH), (Found: C, 66.68; H, 5.73: N, 6.03%, $C_{13}H_{13}NO_3$. $0.2 H_2O$ requires C, 66.55; H, 5.75; N, 5.97%).

EXAMPLE 8

7-(1-Methylethyl)-4-oxo-1,4-dihydroquinoline-2-carboxylic acid

Treatment of ethyl 7-(1-methylethyl)-4-oxo-1,4-dihydroquinoline-2-carboxylic acid (0.5 g) with sodium hydroxide (0.308 g), as described in Example 1c, gave 7-(1-methylethyl)-4-oxo-1,4-dihydroquinoline-2-carboxylic acid (0.378 g), mp>240° C., δ (360 MHz, DMSO-d6) 1.25 (6H, d, $(CH_3)_2$), 2.98 (1H, m, CH), 6.58 (1H, s, 3-H), 7.27 (1H, dd, 6-H), 7.82 (1H, s, 8-H) and 8.00 (1H, d, 5-H), (Found: C, 67.40; H, 5.63; N, 6.44%. $C_{13}H_{13}NO_3$ requires C, 67.52; H, 5.67; N, 6.06%).

EXAMPLE 9

5-Ethenyl-4-oxo-1,4-dihydroquinoline-2-carboxylic acid a) Treatment of 3-nitrobenzaldehyde (20 g) with methyltriphenylphosphonium bromide (61.5g) and n-butyllithium in hexane (172 mmol), as described in Example 1a, gave 3-ethenylnitrobenzene (10.3 g), δ (360 MHz, $CDCl_3$), 5.44 and 5.59 (2H, 2d, $CH_2$), 6.75 (1H, dd, CH), 7.49 (1H, t, 5-H), 7.70 (1H, dd, 4-H), 8.09 (1H, dd, 6-H) and 8.24 (1H, d, 2-H).

To a solution of the above 3-ethenylnitrobenzene (10 g) in acetic acid (30 ml) was added zinc powder (10 g) and the mixture heated to 70° C. with stirring for two hours, then cooled to room temperature and filtered. Ethyl acetate (300 ml) was added to the filtrate, followed by 1M sodium hydroxide until pH 10. The organic layer was separated, washed with water (100 ml), brine (100 ml) and dried over magnesium sulphate. The solvent was removed under reduced pressure to give the crude product, which was purified by column chromatography to give 3-ethenylaniline (4.9 g), δ (60 MHz, $CDCl_3$) 3.60 (2H, bs, $NH_2$), 5.1, 5.2, 5.5 and 5.8 (3H, 4d, $CH_2$ and CH) and 6.3 to 7.3 (4H, m, ArH).

b) Treatment of 3-ethenylaniline (7 g) with diethylacetylene dicarboxylate (9.4 g), as described in Example 1b, gave ethyl 5-ethenyl-4-oxo-1,4-dihydroquinoline-2-carboxylate (0.16 g), mp 168°-170° C., δ (360 MHz, DMSO-d6) 1.37 (3H, t, $CH_3$), 4.41 (2H, q, $CH_2$), 5.25 and 5.55 (2H, 2dd, $=CH_2$), 6.56 (1H, s, 3H), 7.38 (1H, d, 6-H), 7.62 (1H, t, 7-H), 7.90 (1H, d, 8-H), 8.15 (1H, 2d, CH=) and 11.87 (1H, bs, NH) and ethyl 7-ethenyl-4-oxo-1,4-dihydroquinoline-2-carboxylate (0.46 g), mp 177°-179° C., δ (360 MHz, DMSO-d6) 1.37 (3H, t, $CH_3$),4.42 (2H, q, $CH_2$), 5.47 and 5.99 (2H, 2d, $=CH_2$), 6.65 (1H, bs, 3-H), 6.84 (1H, 2d, CH=), 7.54 (1H, d, 6-H) and 7.93 (1H, s, 8-H), 8.04 (1H, d, 5-H), 11.97 (1H, bs, NH).

c) Treatment of ethyl 5-ethenyl-4-oxo-1,4-dihydroquinoline-2-carboxylate (0.15 g) with sodium hydroxide (0.1 g), as described in Example 1c, gave 5-ethenyl-4-oxo-1,4-dihydroquinoline-2-carboxylic acid (0.094 g), mp 265°-266° C., δ (360 MHz, DMSO-d6) 5.24 and 5.54 (2H, 2dd, $=CH_2$), 6.56 (1H, s, 3-H), 7.37 (1H, d, 6-H), 7.62 (1H, t, 7-H), 7.91 (1H, d, 8-H), 8.17 (1H, 2d, CH=) and 11.80 (1H, bs, NH), (Found: C, 66.43; H, 4.37; N, 6.37%, $C_{12}H_9NO_3$. $0.1 H_2O$ requires C, 66.35; H, 4.36; N, 6.44%).

EXAMPLE 10

7-Ethenyl-4-oxo-1,4-dihydroquinoline-2-carboxylic acid

Treatment of ethyl 7-ethenyl-4-oxo-1,4-dihydroquinoline-2-carboxylate (0.2 g) with sodium hydroxide (0.131 g), as described in Example 1c, gave 7-ethenyl-4-oxo-1,4-dihydroquinoline-2-carboxylic acid (0.135 g), mp 281° C. (decomp.), δ (360 MHz, DMSO-d6), 5.47 and 6.00 (2H, 2d, $=CH_2$), 6.61 (1H, s, 3-H), 6.84 (1H, 2d, CH=), 7.54 (1H, dd, 6-H), 7.94 (1H, d, 8-H), 8.05 (1H, d, 5-H) and 11.90 (1H, bs, NH), (Found: C, 63.76; H, 4.48; N, 6.12%, $C_{12}H_9NO_3$. $0.6 H_2O$ requires C, 63.77; H, 4.55; N, 6.20%).

EXAMPLE 11

7-Bromo-5-methyl-4-oxo-1,4-dihydroquinoline-2-carboxylic acid a) A solution of 3-bromo-5-nitrotoluene (21 g, prepared by the method of R. B. Carlin and G. E. Foltz, *J. Amer. Chem. Soc.*, 1956, 78, 1992) in ethanol (250 ml) containing acetic acid (40.8 g) and iron powder (19.0 g) was refluxed with stirring for 3 h. Additional iron powder (9.5 g) was added, and the reaction mixture refluxed a further 3 h, cooled, and added to excess water. The mixture was filtered and the aqueous filtrate extracted with diethyl ether. The organic layer was extracted with 1N hydrochloric acid, the acid extracts basified with sodium hydroxide and the mixture extracted with diethyl ether. The organic extract was dried and evaporated to give 3-bromo-5-methylaniline (15.6 g) which without further purification was dissolved in methanol (200 ml) containing dimethyl acetylene dicarboxylate (11.37 g). The solution was refluxed for 16 hr, evaporated to dryness, and the residue taken up in ether and washed with dilute hydrochloric acid. Evaporation of the ether gave the intermediate enamine (26.1 g) which was added dropwise to stirring diphenyl ether (250 ml) at 250° C. After 15 minutes, the mixture was allowed to cool to room temperature, the crystalline product collected and recrystallised from acetic acid to give a mixture of the 5,7-regioisomers (23 g). This mixture (5 g) was separated by chromatography on silica gel, eluting with dichloromethane/methanol (94:6) to give methyl 7-bromo-5-methyl-4-oxo-1,4-dihydroquinoline-2-carboxylate (0.50 g), mp 270°–271° C., $\delta$ (360 MHz, DMSO-d6) 2.75 (3H, s, $CH_3$), 3.95 (3H, s, $OCH_3$), 6.51 (1H, s, 3-H), 7.24 (1H, d, 6-H) and 7.99 (1H, d, 8-H) (NOE to 6-H only on irradiation of 5-$CH_3$ confirms regiochemistry); and methyl 5-bromo-7-methyl-4-oxo-1,4-dihydroquinoline-2-carboxylate (0.18 g), mp 258°–9° C., $\delta$ (360 MHz, DMSO-d6) 2.37 (3H, s, $CH_3$), 3.95 (3H, s, $OCH_3$) 6.58 (1H, s, 2-H), 7.41 (1H, d, 6-H) and 7.72 (1H, d, 8-H) (NOE to both 6-H and 8-H on irradiation of 7-$CH_3$ confirms regiochemistry).

b) A solution of methyl-7-bromo-5-methyl-4-oxo-1,4-dihydroquinoline-2-carboxylate (0.40 g) in water (10 ml) containing sodium hydroxide (0.22 g) was refluxed for 10 minutes, then acidified with cHCl. The precipitate was collected and recrystallised from $H_2O$/EtOH/-NaOH on addition of cHCl to give 7-bromo-5-methyl-4-oxo-1,4-dihydroquinoline-2-carboxylic acid (0.35 g), mp 299° C. (dec.). m/e 283, 281 (M+); $\delta$ (360 MHz, NaOD-$D_2O$) 2.86 (3H, s, $CH_3$), 6.85 (1H, s, 3-H), 7.22 (1H, d, 6-H) and 7.83 (1H, d, 8-H).

EXAMPLE 12

5-Bromo-7-methyl-4-oxo-1,4-dihydroquinoline-2-carboxylic acid

Methyl 5-bromo-7-methyl-4-oxo-1,4-dihydroquinoline-2-carboxylate (0.14 g) was hydrolysed as described in Example 11b to give 5-bromo-7-methyl-4-oxo-1,4-dihydroquinoline-2-carboxylic acid (0.12 g) mp 298° C. (dec.). m/e 281, 283 (M+); $\delta$ (360 MHz, NaOH-$D_2O$) 2.38 (3H, s, $CH_3$), 6.88 (1H, s, 3-H), 7.45 (1H, d. 6-H) and 7.54 (1H, d, 8-H).

EXAMPLE 13

7-Bromo-5-ethyl-4-oxo-1,4-dihydroquinoline-2-carboxlic acid a) To acetic anhydride (160 ml) at room temperature was added 4-ethylaniline (30 g) over 15 minutes with stirring. The mixture was cooled to 10° C. and concentrated nitric acid (45 ml) was added very slowly, keeping the reaction temperature to below 14° C. The mixture was warmed to room temperature over one hour, poured into ice-water and the resultant yellow solid was filtered off and dried. This was added to dioxan (100 ml), followed by 6M hydrochloric acid (100ml), the solution heated to 70° C. for 3 hr, poured into water, and 1M sodium hydroxide added until pH 10. The product was extracted into ethyl acetate which was then washed with water, brine, dried over magnesium sulphate and solvent removed under vacuum to give 4-ethyl-2-nitroaniline (28.4 g). $\delta$ (60 MHz $CDCl_3$) 1.2 (3H, t, $CH_3$), 2.5 (2H, q, $CH_2$). 6.3 (2H. bs, $NH_2$) and 6.6 to 7.8 (3H, m, ArH).

b) To a solution of 4-ethyl-2-nitroaniline (28 g) in acetic acid (250 ml) was added bromine (9.64 ml) dropwise with stirring at room temperature. The reaction mixture was stirred for 1 hour, poured into water, and extracted with ethyl acetate (3×200 ml). The organic layer was washed with water (3×200 ml), brine (2×100 ml), dried over magnesium sulphate and evaporated to yield 2-bromo-4-ethyl-6-nitroaniline (38 g). This was dissolved in ethanol (200 ml), concentrated sulphuric acid (24 ml) was added dropwise, the mixture heated to reflux and solid sodium nitrate (27 g) added in small amounts over 30 minutes. The reaction mixture was refluxed for a further 1 hour, cooled and poured into ice water. The product was extracted into ethyl acetate which was washed with water (2×100 ml). brine (2×100 ml), dried over magnesium sulphate and evaporated to yield 3-bromo-5-ethyl-nitrobenzene (35.5 g), $\delta$ (60 MHz, $CDCl_3$), 1.3 (3H, t, $CH_3$), 2.8 (2H, q, $CH_2$) 7.6 (1H, s, 4-H), 7.9 (1H, s. 6-H) and 8.0 (1H, s, 2H).

c) To a solution of 3-bromo-5-ethyl nitrobenzene (35 g) in acetic acid (500 ml) was added iron powder (29.77 g) at room temperature. This mixture was refluxed with stirring for 4 hours, then filtered and poured into water (500 ml), and extracted with ethyl acetate (3×200 ml). The combined organic layers were washed with water (200 ml), brine (200 ml), dried over magnesium sulphate and the solvent removed under reduced pressure to yield 3-bromo-5-ethylacetanilide. This crude product was dissolved in dioxan (100 ml), 6N hydrochloric acid added and the solution heated to 80° C. for 3 hours. The reaction mixture was poured into ice water (500 ml), and 1M sodium hydroxide added until pH 10. The product was extracted into ethyl acetate (3×200 ml), the combined organic layers washed with water (2×200 ml), brine (2×200 ml), dried over magnesium sulphate and solvent removed under reduced pressure to yield 3-bromo-5-ethylaniline (14.9 g). $\delta$ (360 MHz, $CDCl_3$) 1.85 (3H, t, $CH_2$), 2.50 (2H, q, $CH_2$), 3.65 (2H, bs, $NH_2$), 6.42 (1H, d, 6-H), 6.65 (1H, d, 3-H) and 6.73 (1H, d, 4-H).

d) Treatment of 3-.bromo-5-ethylaniline (14.5 g), with diethylacetylene dicarboxylate (10.6 ml) as described in Example 1b, gave a mixture of the two 5,7-regioisomers (14.5 g). This mixture (5 g) was separated using column chromatography to give ethyl 7-bromo-5-ethyl-4-oxo-1,4-dihydroquinoline-2-carboxylate (0.9 g), mp 220°–222° C. δ (360 MHz, DMSO-d6) 1.16 (3H, t, CH$_2$CH$_3$), 1.36 (3H, t, CO$_2$ CH$_2$ CH$_3$), 3.24 (2H, q, CH$_2$CH$_3$), 4.41 (2H, q, CO$_2$CH$_2$), 6.57 (1H, s, 3-H), 7.24 (1H, d, 8-H), 8.03 (1H, d, 6-H), 11.79 (1H, bs) and ethyl 5-bromo-7-ethyl-4-oxo-1,4-dihydroquinoline-2-carboxylate (1.1 g), mp 188°–189° C. δ (360 MHz, DMSO-d6) 1.21 (3H, t, CH$_2$CH$_3$), 1.34 (3H, t, CO$_2$CH$_2$CH$_3$), 2.67 (2H, q, CH$_2$CH$_3$), 4.40 (2H, q, CO$_2$CH$_2$), 6.57 (1H, s, 3-H), 7.44 (1H, d, 6-H), 7.78 (1H, d, 8-H) and 11.81 (1H, bs, NH).

e) Treatment of ethyl 7-bromo-5-ethyl-4-oxo-1,4-dihydroquinoline-2-carboxylate with sodium hydroxide (0.247 g), as described in Example 1c, gave 7-bromo-5-ethyl-4-oxo-1,4-dihydroquinoline-2-carboxylic acid, mp 278° C. (decomp.). δ (360 MHz, DMSO-d6) 1.14 (3H, t, CH$_3$), 3.24 (2H, q, CH$_2$), 6.55 (1H, s, 3-H), 7.22 (1H, d, 6-H), 8.02 (1H, d, 8-H) and 11.74 (1H, bs, NH).

EXAMPLE 14

5-Bromo-7-ethyl-4-oxo-1,4-dihydroquinoline-2-carboxylic acid

Treatment of ethyl 5-bromo-7-ethyl-4-oxo-1,4-dihydroquinoline-2-carboxylate (0.59 g) with sodium hydroxide (0.247 g). as described in Example 1a, gave 5-bromo-7-ethyl-4-oxo-1,4-dihydroquinoline-2-carboxylic acid (0.378 g), mp 276° C. (dec.) δ (360 MHz, DMSO-d6) 1.21 (3H, t, CH$_3$), 2.66 (2H, q, CH$_2$), 6.54 (1H, s, 3-H), 7.79 (1H, d, 8-H) and 11.75 (1H, bs, NH), (Found: C, 46.17; H, 3.76; N, 4.48%, C$_{12}$H$_{10}$BrNO$_3$. 0.9H$_2$O requires C, 46.14; H, 3.80; N, 4.48%).

EXAMPLE 15

5-Iodo-4-oxo-1,4-dihydroquinoline-2-carboxylic acid.

3-Iodoaniline (2.4 ml, 0.02 mol) and dimethylacetylene dicarboxylate (1.82 ml, 0.02 mol) were dissolved in dry methanol (100 ml) and heated at reflux for 14 h. The solvent was removed by evaporation and the oily residue partitioned between diethyl ether and 1N hydrochloric acid. The organic layer was dried (Na$_2$SO$_4$), filtered and concentrated in vacuo to leave an oil which was added to diphenyl ether heated to 250° C. After 15 minutes the reaction mixture was allowed to cool to room temperature and triturated with hexane to give a solid which was recrystallised first from acetic acid, then from pyridine, to give the known 7-iodo isomer (1.1 g). The mother liquors were concentrated in vacuo to give a dark yellow solid; repeated recrystallisation from ethanol gave 0.15 g of a material which was pure by t.l.c. This was dissolved in water (60 ml) and ethanol (30 ml) with sodium hydroxide (0.15 g) and heated at 100° C. for 1 h. Addition of 1N hydrochloric acid to pH 1 caused precipitation of a yellow solid which was collected by filtration and washed successively with water, ethanol and diethyl ether, to give 5-iodo-4-oxo-1,4-dihydroquinoline-2-carboxylic acid (0.083 g), m.p. 286°–287° C. (dec), δ (360 MHz, NAOD) 6.75 (1H, s, 3-H), 7.08 (1H, t, 7-H), 7.66 (1H, d, 8-H) and 7.87 (1H, d, 6H). (Found: C, 36.90; H, 1.98; N. 4.33% C$_{10}$H$_6$INO$_3$.0.5H$_2$O requires C, 37.06; H, 2.18; N, 4.32%).

EXAMPLE 16

5-Fluoro-4-oxo-1,4-dihydroquinoline-2-carboxylic acid

Using the method described in Example 15 with 3-fluoroaniline (8.7 ml) and dimethylacetylene dicarboxylate (5.46 ml) gave 5-fluoro-4-oxo-1,4-dihydroquinoline-2-carboxylic acid (0.022 g), m.p. 285°–286° C. (dec), δ (360 MHz, NAOD) 6.86 (1H, s, 3-H), 7.04 (1H, m, 7-H) and 7.52–7.68 (2H. m, 6-H, 8-H).

EXAMPLE 17

5-Trifluoromethyl-4-oxo-1,4-dihydroquinoline-2-carboxylic acid

Using the method described in Example 15 with 3-aminobenzotrifluoride (40 g) and dimethylacetylene dicarboxylate (35 g) gave 5-trifluoromethyl-4-oxo-1,4-dihydroquinoline-2-carboxylic acid (0.04 g) m.p. 265°–267° C. (dec), δ (360 MHz, DMSO-d6) 6.65 and (1H, s, 3-H), 7.78 (2H, m, 7-H, 8-H), 8.26 (1H, d, 6-H) and 12.08 (1H, N-H).

EXAMPLE 18

5,6,7-Trichloro-4-oxo-1,4-dihyvdroquinoline-2-carboxylic acid a) 3,4,5-Trichloroaniline (25 g, 0.127 mol) and dimethylacetylene dicarboxylate (10.9 ml, 0.12 mol) were dissolved in dry methanol (300 ml) at 0° C. then heated at reflux for 14 h. The mixture was allowed to cool, then diluted with hexane (200 ml) and the yellow solid which precipitated was collected by filtration and heated in diphenyl ether (200 ml) at 240° C. for 10 minutes. The reaction mixture was allowed to cool to room temperature and diluted with hexane. The solid which deposited was collected and recrystallised from acetone (500 ml) to give methyl 5,6,7-trichloro-4-oxo-1,4-dihydroquinoline-2-carboxylate (11.91 g), m.p. 295°–296° C. (decomp), δ (360 MHz, DMSO-d6) 3.96 (3H, s, CH$_3$), 6.63 (1H, s, 3-H) and 8.17 (1H, s, 8-H) (Found C, 43.09; H, 1.70; N, 4.47%, C$_{11}$H$_{16}$NO$_3$Cl$_3$ requires C, 43.10; H, 1.97; N, 4.57%).

b) Treatment of methyl 5,6,7-trichloro-4-oxo-1,4-dihydroquinoline-2-carboxylate (3 g) with sodium hydroxide (1.57 g) as described in Example 1c, gave 5,6,7-trichloro-4-oxo-1,4-dihydroquinoline-2-carboxylic acid (2.15 g). m.p. 290° C. (dec), δ (360 MHz, NAOD) 6.69 (1H, s, 3-H) and 7.66 (1H, s, 8-H) (Found: C, 40.90; H, 1.15; N, 4.78%, C$_{10}$H$_4$NO$_3$Cl$_3$ requires C, 41.06; H, 1.38; N, 4.79%).

EXAMPLE 19

6-Trifluoromethyl-4-oxo-1,4-dihydroquinoline-2-carboxylic acid a) Using the method described in Example 18a with 4-aminobenzotrifluoride (20 g) and dimethylacetylene dicarboxylate (17.5 g) as reagents gave methyl 6-trifluoromethyl-4-oxo-1,4-dihydroquinoline-2-carboxylate (0.91 g), m.p. 289°–291° C., δ (360 MHz, DMSO-d6) 3.98 (3H, s, CH$_3$), 6.74 (1H, s, 3-H), 8.02 (1H, dd, 7-H), 8.13 (1H, d, 8-H), 8.33 (1H, s, 5-H) and 12.40 (1H, s, NH).

b) Treatment of methyl 6-trifluromethyl-4-oxo-1,4-dihydroquinoline-2-carboxylate (0.5 g. Example 19a) with sodium hydroxide (0.295 g), as described in Example 1c, gave 6-trifluoromethyl-4-oxo-1,4-dihydroquinoline-2-carboxylic acid (0.21 g), m.p. 287°–289° C., δ (360 MHz, DMSO-d6) 6.72 (1H, s, 3-H), 8.01 (1H, dd, 7-H), 8.14 (1H, d, 8-H), 8.33 (1H, s, 5-H). (Found: C, 49.11; H. 2.79; N, 5.12%; C$_{11}$H$_6$NO$_3$. 0.75H$_2$O requires C, 48.81; H, 2.79; N, 5.17%).

EXAMPLE 20

6-Methylthio-4-oxo-1,4-dihydroquinoline-2-carboxylic acid a) Using the method described in Example 18a with 4-methylthioaniline (20 g) and dimethyl-acetylene dicarboxylate (20.21 g) as reagents gave methyl 6-methylthio-4-oxo-1,4-dihydroquinoline-2-carboxylate (10.12 g), m.p. 264°–266° C. δ (360 MHz, DMSO-d6), 2.55 (3H, s, CH$_3$S), 3.96 (3H, s, CH$_3$O), 6.68 (1H, s, 3-H), 7.64 (1H, dd, 7-H), 7.83 (1H, d, 5-H) and 7.89 (1H, d, 8-H).

b) Treatment of methyl 6-methylthio-4-oxo-1,4-dihydroquinoline-2-carboxylate (2.0 g) with sodium hydroxide (1.29 g), as described in Example 1c, gave 6-methylthio-4-oxo-1,4-dihydroquinoline-2-carboxylic acid (1.6 g), m.p. 256°–257° C. δ (360 MHz, DMSO-d6) 2.55 (3H, s, CH$_3$S), 6.65 (1H, s, 3-H), 7.62 (1H, dd, 7-H), 7.83 (1H, d, 5-H) and 7.90 (1H, d, 8-H). (Found: C, 54.08; H, 4.19; N, 5.72% C$_{11}$H$_9$NO$_3$S.0.5H$_2$O requires C, 54.09; H. 4.13; N. 5.72%)

EXAMPLE 21

5,7-Dimethyl-4-oxo-1,4-dihydroquinoline-2-carboxylic acid a) Using the method described in Example 18a with 3,5-dimethylaniline (20 g) and dimethylacetylene dicarboxylate (23.4 g) as reagents gave methyl 5,7-dimethyl-4-oxo-1,4-dihydroquinoline-2-carboxylate (1.25 g), m.p. 227°–229° C. δ (360 MHz, DMSO-d6) 2.34 (3H, s, 7-Me), 2.74 (3H, s, 5-Me), 3.94 (3H, s, CH$_3$O), 6.49 (1H, s, 3-H), 6.89 (1H, s, 6-H) and 7.54 (1H, s, 8-H).

b. Treatment of methyl 5,7-dimethyl-4-oxo-1,4-dihydroquinoline-2-carboxylate (1 g) with sodium hydroxide (0.69 g), as described in Example 1c, gave 5,7-dimethyl-4-oxo-1,4-dihydro-quinoline-2-carboxylic acid (0.8 g), m.p. 285°–287° C., δ (360 MHz,DMSO-d6) 2.33 (3H, s, 7-Me), 2.75 (3H. s, 5-Me), 6.49 (1H, s, 3-H), 6.87 (1H, s, 6-H) and 7.55 (1H, s, 8-H). (Found: C, 66.53; H, 4.96; N, 6.72%. C$_{12}$H$_{11}$NO$_3$ requires C, 66.35; H, 5.10; N,6. 45%).

EXAMPLE 22

5-Cyano-4-oxo-1,4-dihydroquinoline-2-carboxylic acid

3-Cyanoaniline (21.3 g, 0.18 mol) and dimethylacetylene dicarboxylate (10.9 ml, 0.12 mol) were dissolved in dry methanol and heated at reflux for 14 h. After cooling, the solvent was removed in vacuo and the residue partitioned between diethyl ether and 1N hydrochloric acid. The organic layer was dried (Na$_2$SO$_4$), filtered and concentrated in vacuo to leave an oil which was heated in diphenyl ether (100 ml) at 250° C. for 15 minutes. On cooling, a solid precipated which was collected and recrystallised successively from acetic acid/diethyl ether, then from pyridine, to give a pure material by t.l.c. (0.165 g). This was dissolved in water (20 ml) and methanol (10 ml) with sodium hydroxide (0.13 g) and the solution heated at 100° C. for 2 h. Addition of 1N hydrochloric acid caused precipitation of a white solid which was collected by filtration and washed successively with water, ethanol and diethyl ether to give 5-cyano-4-oxo-1,4-dihydroquinoline-2-carboxylic acid (0.14 g) m.p. 278°–279° C., δ (360 MHz, NAOD) 6.96 (1H, s, 3-H), 7.64 (1H, dd, 7-H), 7.83 (1H, dd, 6-H) and 8.05 (1H, dd, 8-H). (Found: C, 60.23; H, 3.03; N, 12.46%. C$_{11}$H$_6$N$_2$O$_3$. 0.3H$_2$O requires C, 60.17; H, 3.03; N, 12.78%).

EXAMPLE 23

5-Hydroxy-4-oxo-1,4-dihydroquinoline-2-carboxylic acid

3-Aminophenol (10.0 g) was dissolved in dichloromethane (200 ml), cooled to −50° C. and dimethyl-acetylene dicarboxylate (12.93 g) added. The reaction mixture was allowed to warm to room temperature and stirred for 3 days. The solvent was evaporated to leave a yellow oil (20 g). A portion of this oil (3 g) was heated in diphenyl ether (250 ml) at 210° C. for 10 minutes and allowed to cool to room temperature. Addition of hexane caused precipitation of a solid which was purified by chromatography on silica gel, eluting with 5% methanol in dichloromethane to give a yellow solid (0.25 g). This was dissolved in water (15 ml) and ethanol (7 ml) with sodium hydroxide (0.073 g) and the solution stirred for 4 h at room temperature. Addition of 1N hydrochloric acid caused precipitation of a solid which was collected by filtration and washed successively with hot water, ethanol and diethyl ether to give 5-hydroxy-4-oxo-1,4-dihydroquinoline-2-carboxylic acid (0.2 g), m.p. 298°–301° C., δ (360 MHz, DMSO-d6) 6.60 (1H, dd, 6-H), 6.62 (1H, s, 3-H), 7.34 (1H, dd, 8-H) and 7.54 (1H, t, 7-H). (Found: C, 57.72; H, 3.67; N, 6.67%. C$_{10}$H$_7$NO$_4$.0.2H$_2$O requires C, 57.53; H, 3.57; N, 6.71%).

EXAMPLE 24

5,7-Dichloro-4-oxo-1,4-dihydroquinoline-2-hydroxamic acid potassium salt.

Hydroxylamine hydrochloride (0.51 g) was dissolved in hot methanol (5 ml) and added to a solution of potassium hydroxide (0.62 g) in methanol (10 ml) at 30° C. The reaction mixture was cooled to 0° C. and after stirring for 15 minutes, filtered through a sinter funnel directly onto methyl 5,7-dichloro-4-oxo-1,4-dihydroquinoline-2-carboxylate (1 g, prepared by the method of N. D. Heindel et al, *J. Med. Chem.*, 1968, 11, 1218). After stirring for 6 days at room temperature the yellow solid that was precipitated was collected by filtration, heated in refluxing methanol and again collected by filtration to give 5,7-dichloro-4-oxo-1,4-dihydroquinoline-2-hydroxamic acid potassium salt (0.64 g), m.p. 257° C. (dec), δ (360 MHz, DMSO-d6) 6.39 (1H, s, 3-H) 7.06 (1H, s, 6-H) and 7.72 (1H, s, 8-H). (Found: C, 37.64; H, 1.59; N, 8.68%. C$_{10}$H$_5$Cl$_2$N$_2$O$_3$K.0.5H$_2$O requires C, 37.51; H, 1.89; N, 8.75%).

EXAMPLE 25

5,7-Dichloro-4-oxo-1,4-dihydroquinoline-2-(O-benzyl) hydroxamic acid 5,7-Dichloro-4-oxo-1,4-dihydroquinoline-2-carboxylic acid (1 g) and carbonyl diimidazole (0.38 g, 0.0023 mol) were dissolved in tetrahydrofuran (150 ml) and dimethyformamide (50 ml) and the solution heated at 60° C. for 1.5 h. O-Benzylhydroxylamine hydrochloride (0.37g, 0.0023 mol) was added and the reaction heated for a further 0.5 h. The reaction mixture was allowed to cool and the solvents removed in vacuo to leave a residue which was triturated with dichloromethane and the solid collected by filtration. This product was heated in refluxing methanol and filtered while hot to give, as a white solid, 5,7-dichloro-4-oxo-1,4-dihydroquinoline-2-

(O-benzyl)hydroxamic acid (0.55 g), m.p. 277° C. (dec), δ (360 MHz, DMSO-d6), 4.96 (2H, s, CH2), 6.52 (1H, s, 3-H), 7.42 (6-H, m, 6-H and ArH) and 7.95 (1H, s, 8-H). (Found: C, 56.04; H, 3.06; N, 7.88%. $C_{17}H_{12}Cl_2N_2O_3$ requires C, 56.22; H, 3.33; N, 7.71%).

EXAMPLE 26

5,7-Dichloro-4-oxo-1,4-dihydroquinoline-2-carboxamide

Methyl 5,7-dichloro-4-oxo-1,4-dihydroquinoline-2-carboxylate (1 g) was dissolved in methanol (400 ml) and the solution filtered. After cooling to 0° C., ammonia was bubbled through the solution for 0.5 h and the reaction mixture was kept at 4° C. for 10 days. The solvent was removed in vacuo and the residue recrystallised from methanol to give 5,7-dichloro-4-oxo-1,4-dihydroquinoline-2-carboxamide (0.13 g). m.p. 323° C. (dec), δ (360 MHz, DMSO-d6) 6.79 (1H, s, 3-H), 7.39 (1H, s, 6-H), 8.02 (1H, s, 8-H), 8.12 (1H, s, $NH_1H_2$), 8.47 (1H, s, $NH_1H_2$) and 11.77 (1H, s, NH). (Found: C, 46.59; H, 2.30; N, 11.08%. $C_{10}H_6Cl_2N_2O_2$ requires C, 46.72; H, 2.35; N, 10.90%).

EXAMPLE 27

7-Chloro-5-ethyl-4-oxo-1,4-dihydroquinoline-2-carboxylic acid a) To a stirred solution of 4-ethyl-2-nitroaniline (26.3 g, Example 13a) in DMF (100 ml) at −25° C. was added N-chlorosuccinimide (25.4 g) in portions. The mixture was stirred for 1 h at 0° C. and 30 minutes at ambient temperature before evaporation of the solvent under vacuum. Addition of $CHCl_3$/hexane (1:1) to the residue followed by filtration removed crystalline succinimide. 6-Chloro-4-ethyl-2-nitroaniline (4.6 g) was isolated from the filtrate after chromatography on silica. δ (360 MHz, CDCl3) 1.22 (3H, t, CH3), 2.56 (2H, q, CH2), 6.38 (2H. s, NH2), 7.4 (1H, d, 5-H) and 7.90 (1H, s, 3-H).

b) To 6-chloro-4-ethyl-2-nitroaniline (5.3 g) in ethanol (40 ml) was added c.$H_2SO_4$ (5 ml) dropwise. The solution was heated to reflux and solid $NANO_2$ (4.55 g) was added in small portions over 25 minutes. After a further 1 h at reflux the mixture was poured onto ice and extracted with ethyl acetate. The organic phase was washed with water (×3) and brine (×3), dried over MGSO4 and evaporated. 3-Chloro-5-ethylnitrobenzene was isolated as a yellow oil (4.0 g) after silica chromatography. δ (60 MHz, CDCl3) 1.2 (3H, t, CH3), 2.5 (2H, q, CH2), 7.5 (1H, s, Ar) and 7.9 (2H, s, Ar). This product was treated with iron powder (2.7 g) in acetic acid (40 ml) and ethanol (30 ml) at reflux for 2.5 h. The mixture was filtered through celite and the solvent evaporated. The residual oil was diluted with hexane (2 ml) and chromatographed on silica, eluting with 20% $CHCl_3$/hexane. 3-Chloro-5-ethylaniline (0.9 g) was isolated as a pure oil. δ (360 MHz, CDCl3) 1.19 (3H, t, CH3), 2.52 (2H, q, CH2), 3.20 (2H, s, NH2), 6.38 (1H, dd, Ar), 6.49 (1H, dd, Ar) and 6.58 (1H, dd, Ar).

c) Reaction of 3-chloro-5-ethylaniline (0.9 g) with diethylacetylene dicarboxylate (0.93 ml) as described in Example 1b gave a mixture of the two 5,7-regioisomers (800 mg). The isomers were separated by silica chromatography to give ethyl 7-chloro-5-ethyl-4-oxo-1,4-dihydroquinoline-2 -carboxylate (250 mg), mp 222°-3° C.; δ (360 MHz, DMSO-d6) 1.15 (3H, t, CH2CH3), 1.36 (3H, t, CO2CH2CH3), 3.25 (2H, q, CH2CH3), 4.42 (2H, q, CO2CH2) 6.57 (1H, s, 3-H), 7.12 (1H, d, 8-H), 7.87 (1H, d, 6-H) and 11.75 (1H, bs, NH); and ethyl 5-chloro-7-ethyl-4-oxo-1,4-dihydroquinoline-2-carboxylate (200 mg), mp 182°-3° C.; δ (360 MHz, DMSO-d6) 1.21 (3H, t, CH2CH3), 1.35 (3H, t, CO2CH2CH3), 2.67 (2H, q, CH2CH3), 4.40 (2H, q, CO2CH2) 6.56 (1H, s, 3-H), 7.28 (1H, d, 6-H), 7.73 (1H, d, 8-H) and 11.78 (1H, bs, NH).

d) Treatment of ethyl 7-chloro-5-ethyl-4-oxo-1,4-dihydroquinoline-2-carboxylate (250 mg) with 2M is NAOH (1.5 ml) in DMF at room temperature for 76 h, followed by acidification with HCl, gave 7-chloro-5-ethyl-4-oxo-1,4-dihydroquinoline-2-carboxylic acid (222 mg), mp 282°-283° C. δ (360 MHz, DMSO-d6) 1.15 (3H, t, CH3), 3.26 (2H, q, CH2), 6.55 (1H, s, 3-H), 7.10 (1H, d, 6-H), 7.88 (1H, d, 8-H) and 11.78 (1H, bs, NH).

EXAMPLE 28

5-Chloro-7-ethyl-4-oxo-1,4-dihydroquinoline-2-carboxylic acid

Treatment of ethyl-5-chloro-7-ethyl-4-oxo-1,4-dihydroquinoline-2-carboxylate (200 mg) with 2M NAOH (1.2 ml) as described in Example 27d yielded 5-chloro-7-ethyl-4-oxo-1,4-dihydroquinoline-2-carboxylic acid (150 mg), mp 248°-250° C. δ (360 MHz, DMSO-d6) 1.21 (3H, t, CH3), 2.66 (2H, q, CH2), 6.52 (1H, s, 3-H), 7.20 (1H, d, 6-H), 7.75 (1H, d, 8-H) and 11.76 (1H, bs, NH).

EXAMPLE 29

5-Chloro-7-iodo-4-oxo-1,4-dihydroquinoline-2-carboxylic acid a) A solution of 4-chloro-2-nitroaniline (34.5 g) in acetic acid (500 ml) was refluxed with iodine monochloride (65.0 g) for 7 h with stirring, then was cooled and added to excess water. The precipitate was filtered off, washed with aqueous sodium sulphite and after column chromatography yielded 4-chloro-2-iodo-6-nitroaniline (8.5 g). δ (360 MHz, DMSO-d6) 7.13 (2H, bs, NH2), 8.08 (1H, d, 3-H) and 8.13 (1H, d, 5-H).

b) To a solution of 4-chloro-2-iodo-5-nitroaniline (8.5 g) in ethanol (38 ml) was added concentrated sulphuric acid (4.4 ml) dropwise, then the solution was heated to reflux and solid sodium nitrite (4.9 g) added in small amounts over 30 minutes. The mixture was refluxed a further one hour and poured into ice water, the product extracted into ethyl acetate, washed with water and brine and the organic layer was dried over sodium sulfate. The solution was evaporated and the residue purified by column chromatography to give 5-chloro-3-iodonitrobenzene (3.4 g). δ (360 MHz, DMSO-d6) 8.28 (1H, d, 2-H), 8.35 (1H, d, 6-H) and 8.46 (1H, d, 4-H).

c) A solution of 5-chloro-3-iodonitrobenzene (3.45 g) in acetic acid (10 ml) and ethanol (58 ml) containing iron powder (6.4 g) was refluxed for 6 h with stirring, cooled, filtered and poured into water (100 ml). The product was extracted into ethyl acetate, washed with water, dried over magnesium sulfate, filtered and solvent evaporated to yield, after column chromatography, 3-chloro-5-iodoaniline (1.5 g). δ (360 MHz, DMSO-d6) 5.58 (2H, bs, NH2) 6.57 (1H, bs, 6-H), 6.80 (1H, bs, 2-H), and 6.88 (1H, bs, 4-H).

d) Treatment of 3-chloro-5-iodoaniline (1.4 g) with diethylacetylene dicarboxylate (0.93 ml), as described in Example 1b, gave a mixture (1.83 g) of ethyl 5-chloro-7-iodo-4-oxo-1,4-dihydroquinoline-2-carboxylate [δ (360 MHz, DMSO-d6) 1.37 (3H, t, CH2CH3), 4.40 (2H, q, CH2CH3), 6.59 (1H, s, 3-H), 7.61 (1H, s, 6-H), 8.32 (1H, s, 8-H) and 11.90 (1H, bs, NH)] and ethyl 7-chloro-5-iodo-4-oxo-1,4-dihydroquinoline-2-carboxylate [δ (360 MHz, DMSO-d6) 1.37 (3H, t, CH2CH3), 4.40 (2H, q, CH$_2$CH$_3$), 6.63 (1H, s, 3-H), 7.90 (1H, s, 6-H), 8.04 (1H, s, 8-H) and 11.90 (1H, bs, NH)].

e) Treatment of a mixture of ethyl 5-chloro-7-iodo-4-oxo-1,4-dihydroquinoline-2-carboxylate and ethyl 7-chloro-5-iodo-4-oxo-1,4-dihydroquinoline-2-carboxylate (1.0 g) with sodium hydroxide as described in Example 1c, gave a mixture (0.930 g) of 5-chloro-7-iodo-4-oxo-1,4-dihydroquinoline-2-carboxylic acid and 7-chloro-5-iodo-4-oxo-1,4-dihydroquinoline-2carboxylic acid. Chromatography of this mixture (0.150 g) on a reverse phase carbon-18 column gave 5-chloro-7-iodo-4-oxo-1,4-dihydroquinoline-2-carboxylic acid (11 mg), mp 275° C. (dec). δ (360 MHz, DMSO-d$_6$) 6.55 (1H, s, 3-H), 7.62 (1H, d, 6-H), 8.34 (1H, d, 8-H) and 11.91 (1H, bs, NH).

EXAMPLE 30

7-Chloro-5-iodo-4-oxo-1,4-dihydroquinoline-2-carboxylic acid

The RP18 column chromatography described in Example 29e also yielded 7-chloro-5-iodo-4-oxo-1,4-dihydroquinoline-2-carboxylic acid (8 mg). mp 298° C. δ (360 MHz, DMSO-d$_6$) 6.58 (1H, s, 3-H), 7.88 (1H, d, 6-H) 8.09 (1H, d, 8-H) and 11.91 (1H, bs, NH).

EXAMPLE 31

5-Iodo-7-methyl-4-oxo-1,4-dihydroquinoline-2-carboxylic acid a) A solution of 4-amino-3-nitrotoluene (30.4 g) in acetic acid (250 ml) was refluxed with iodine monochloride (65.0 g) for 7 h with stirring, then was cooled and added to excess water. The precipitate was filtered off, washed with aqueous sodium sulfite and after column chromatography yielded 4-amino-3-iodo-5-nitrotoluene (14.2 g). δ (360 MHz, DMSO-d$_6$) 2.19 (3H, s, CH$_3$), 6.88 (2H, bs, NH$_2$), 7.88 (1H, d, 2-H) and 7.94 (1H, d, 6-H).

b) To a solution of 4-amino-3-iodo-5-nitrotoluene (14.0 g) in ethanol (70 ml) was added concentrated sulphuric acid (8 ml) dropwise, then the solution was heated to reflux and solid sodium nitrite (8.9 g) added in small amounts over 30 minutes. The mixture was refluxed a further one hour, and then was poured into ice water. The precipitate was washed with water and dried to yield 3-iodo-5-nitrotoluene (10.2 g). δ (360 MHz, DMSO-d$_6$) 2.40 (3H, s, CH$_3$), 8.07 (2H, bs, 2-H and 6-H) and 8.30 (1H, s, 4-H).

c) Treatment of 3-iodo-5-nitrotoluene (10.0 g) in acetic acid (200 ml) containing iron powder (20.0 g), as described in Example 13c, gave 3-iodo-5-methylacetanilide. Treatment of this product in dioxan (100 ml) with 6N hydrochloric acid, as described in Example 13c, gave, after column chromatography, 3-iodo-5-methylaniline (17.7 g). δ (360 MHz, DMSO-d$_6$) 2.09 (3H, s, CH$_3$), 5.19 (2H, bs, NH$_2$), 6.35 (1H, s, 6-H), 6.64 (1H, s, 2-H) and 6.73 (1H, s, 4-H).

d) Treatment of 3-iodo-5-methylaniline (4.1 g) with diethylacetylene dicarboxylate (2.8 ml) as described in Example 1b, gave a mixture (3.0 g) of ethyl 5-iodo-7-methyl-4-oxo-1,4-dihydroquinoline-2-carboxylate [δ (360 MHz, DMSO-d$_6$) 1.50 (3H, t, CH$_2$CH$_3$), 2.76 (3H, s, CH$_3$), 4.41 (2H, q, CH$_2$CH$_3$), 6.58 (1H, s, 3-H), 7.74 (1H, s, 6-H) and 7.78 (1H, s, 8-H)] and ethyl 7-iodo-5-methyl-4-oxo-1,4-dihydroquinoline-2-carboxylate [δ (360 MHz, DMSO-d$_6$) 1.33 (3H, t, CH$_2$CH$_3$), 2.72 (3H, s, CH$_3$), 4.41 (2H, q, CH$_2$CH$_3$), 6.54 (1H, bs, 3-H), 7.40 (1H, s, 6-H) and 8.20 (1H, s, 8-H)].

e) Treatment of a mixture of ethyl 5-iodo-7-methyl-4-oxo-1,4-dihydroquinoline-2-carboxylate and ethyl 7-iodo-5-methyl-4-oxo-1,4-dihydroquinoline-2-carboxylate (0.449 g) with sodium hydroxide (0.20 g) as described in Example 1c gave a mixture of the corresponding carboxylic acids. Chromatography of this mixture (0.220 g) on a reverse phase carbon-18 column gave 5-iodo-7-methyl-4-oxo-1,4-dihydroquinoline-2-carboxylic acid (12 mg), mp 306° C. δ (360 MHz, DMSO-d$_6$) 2.33 (3H, s, CH$_3$), 6.55 (1H, s, 3-H) and 7.75 (2H, bs, 6-H and 8-H).

EXAMPLE 32

7-Iodo-5-methyl-4-oxo-1,4-dihydroquinoline-2-carboxylic acid

The RP18 column described in Example 31e also yielded 7-iodo-5-methyl-4-oxo-1,4-dihydroquinoline-2-carboxylic acid (80 mg), mp 294° C. δ (360 MHz, DMSO-d$_6$) 2.72 (3H, s, CH$_3$), 6.50 (1H, s, 3-H), 7.37 (1H, s, 6-H) and 8.20 (1H, s, 8-H).

EXAMPLE 33

2-Diethylaminoethyl 5,7-Dichloro-4-oxo-1,4-dihydroquinoline-2-carboxylate hydrobromide a) To a suspension of methyl 5,7-dichloro-1,4-dihydroquinoline-2-carboxylate (3 g) in dry dimethylformamide (20 ml) was added potassium carbonate (6.1 g) followed by benzyl bromide (1.44 ml) and the mixture stirred at room temperature for 16 hours. The reaction mixture was poured into water (100 ml) and extracted with ethyl acetate (3×100 ml), the organic layers were combined and washed with water (2×100 ml), 1M hydrochloric acid (1×100 ml), brine (2×100 ml) and dried over magnesium sulphate. The solvent was removed under reduced pressure and the crude product purified by column chromatography to give methyl 4-benzyloxy-5,7-dichloroquinoline-2-carboxylate (2.8 g). δ (360 MHz, DMSO-d$_6$) 3.95 (3H, s, OCH$_3$), 5.48 (2H, s, CH$_2$), 7.35 (1H, d, p-ArH), 7.38 (2H, t, m-ArH), 7.46 (2H, d, o-ArH), 7.59 (1H, s, 3-H), 7.83 (1H, d, 6-H) and 8.11 (1H, d, 8-H).

b) To a suspension of methyl-4-benzyloxy-5,7-dichloroquinoline-2-carboxylate (1.2 g) in ethanol (20 ml) was added a solution of sodium hydroxide (0.53 g) in water (20 ml) and the mixture was stirred at room temperature for 1 h. Hydrochloric acid (11M) was added until pH2 and the resulting precipitate was filtered off, washed with water (20 ml), ethanol (10 ml), diethylether (5 ml) and dried to yield 4-benzyloxy-5,7-dichloroquinoline-2-carboxylic acid (0.95 g). δ (360 MHz, DMSO-d$_6$), 5.49 (2H, s, CH$_2$), 7.40 (3H, m, m,p-ArH), 7.58 (2H, d, o-ArH), 7.71 (1H, s, 3-H), 7.83 (1H, d, 6-H) and 8.81 (1H, d, 8-H).

c) To 4-benzyloxy-5,7-dichloroquinoline-2-carboxylic acid (1.7 g), was added thionyl chloride (10 ml) and the mixture was heated to reflux for 2 hours. The mixture was cooled to room temperature, excess thionyl chloride removed under reduced pressure to give an off white solid, to which was added dry tetrahydrofuran (20 ml). The solution was cooled to 0° C. and N,N-diethylethanolamine (2.1 ml) added dropwise. The reaction was left to warm to room temperature over 1 hour, poured into 10% sodium carbonate (100 ml) and extracted with ethyl acetate (3×100 ml). The organic layers were combined and washed with water (2×100 ml), brine (2×50 ml) and dried over magnesium sulphate. The solvent was removed under reduced pressure and the crude product purified by column chromatography to give 2-diethylaminoethyl 4-benzyloxy-5,7-dichloroquinoline-2-carboxylate (1.1 g). δ (360 MHz, DMSO-$d_6$), 0.99 (1H, t, $CH_2CH_3$), 2.54 (4H, q, $CH_2CH_3$), 2.81 (2H, t, $CH_2N$), 4.41 (2H, m, $CO_2CH_2$), 5.50 (2H, s, $OCH_2$), 7.41 (3H, m, o,p-ArH), 7.60 (2H, d, m-ArH), 7.71 (1H, s, 3-H), 7.86 (1H, d, 6-H) and 8.12 (1H, d, 8-H).

d) To 2-diethylaminoethyl 4-benzyloxy-5,7-dichloroquinoline-2-carboxylate (0.55 g) at room temperature was added hydrogen bromide in acetic acid (15 ml of a 48% solution) and the solution was stirred in a sealed flask for 48 hours. The reaction mixture was poured into dry ether (50 ml) to give a pale yellow solid which was filtered off and recrystallised from ethanol to yield 2-diethylaminoethyl 5,7-dichloro-4-oxo-1,4-dihydroquinoline-2-carboxylate hydrobromide (0.36 g), m.p. 220° C. (dec). δ (360 MHz, DMSO-$d_6$), 1.25 (6H, t, $CH_3$), 3.28 (4H, m, $NCH_2CH_3$), 3.57 (2H, m, $OCH_2CH_2N$), 4.66 (2H, t, $OCH_2CH_2$), 6.86 (1H, s, 3-H), 7.47 (1H, d, 6-H), 8.05 (1H, d, 8-H), 9.37 (1H, bs, NH) and 12.1 (1H, vbs, NH). (Found: C, 40.20; H, 4.15; N, 5.86%. $C_{16}H_{18}Cl_2N_2O_3$. 1.5HBr requires C, 40.15; H, 4.10; N, 5.85%).

EXAMPLE 34

2-(1-Pyrrolidinyl)ethyl
5,7-dichloro-4-oxo-1,4-dihydroquinoline-2-carboxylate hydrobromide a) Treatment of 4-benzyloxy-5,7-dichloroquinoline-2-carboxylic acid (1 g, Example 33b) with thionyl chloride (10 ml) followed by 1-(2-hydroxyethyl) pyrrolidine (0.43 ml) as described in Example 33c, gave 2-(1-pyrrolidinyl)ethyl 4-benzyloxy-5,7-dichloroquinoline-2-carboxylate (0.7 g). δ (360 MHz, DMSO$d_6$) 1.70 (4H, bs, pyrrolidine-3,4-H), 2.60 (4H, bs, pyrrolidine-2.5-H), 2.88 (2H, t, $CH_2N$), 4.48 (2H, t, $CO_2CH_2$), 5.50 (2H, s, $OCH_2$), 7.38 (3H, m, m,p-ArH), 7.58 (2H, d, o-ArH), 7.71 (1H, s, 3-H), 7.86 (1H, d, 6-H) and 8.13 (1H, d, 8-H).

b) Treatment of 2-(1-pyrrolidinyl)ethyl 4-benzyloxy-5,7-dichloroquinoline-2-carboxylate (0.65 g) with hydrogen bromide in acetic acid (5 ml, 48%) as described in Example 33d gave 2-(1-pyrrolidinyl)ethyl 5,7-dichloro-4-oxo-1,4-dihydroquinoline-2-carboxylate hydrobromide (0.3 g), m.p. 258° C. (dec). δ (250 MHz, DMSO-$d_6$) 2.04 (4H, m, pyrrolidine-3,4-H), 3.18 (2H, m, $CH_2N$) 3.68 (4H, m, pyrrolidine-2.5-H), 4.68 (2H, t, $CO_2CH_2$), 6.91 (1H, s, 3-H), 7.46 (1H, d, 6-H), 8.08 (1H, d, 8-H), 9.90 (2H, vbs, NH). (Found: C, 41.24; H, 3.68; N, 6.03%. $C_{16}H_{16}Cl_2N_2O_3$. 1.35HBr requires C, 41.38; H, 3.76; N, 6.03%).

EXAMPLE 35

3-Dimethylaminopropyl
5,7-dichloro-4-oxo-1,4-dihydroquinoline-2-carboxylate hydrobromide a) Treatment of 4-benzyloxy-5,7-dichloroquinoline-2-carboxylic acid (1 g, Example 33b) with thionyl chloride (10 ml) followed by 3-dimethylamino- 1-propanol (1.1 ml) as described in Example 33c gave 3-dimethylaminopropyl 4-benzyloxy-5,7-dichloroquinoline-2-carboxylate (0.52 g). δ (360 MHz, DMSO-$d_6$) 1.93 (2H, m, $CO_2CH_2CH_2$), 2.20 (6H, s, $(CH_3)_2$), 2.44 (2H, t, $CH_2N$), 4.40 (2H, t, $CO_2CH_2$), 5.50 (2H s, $OCH_2$), 7.34 (3H, m, m,p-ArH), 7.58 (2H, d, 2 ArH), 7.72 (1H, s, 3-H), 7.88 (1H, d, 6-H) and 8.14 (1H, d, 8-H).

b) Treatment of 3-dimethylaminopropyl 4-benzyloxy-5,7-dichloroquinoline-2-carboxylate (0.52 g) with hydrogen bromide in acetic acid (10 ml, 48%) as described in Example 33d gave 3-dimethylaminopropyl 5,7-dichloro-4-oxo-1,4-dihydroquinoline-2-carboxylate hydrobromide (0.27 g), m.p. 228° C. (dec). δ (360 MHz, DMSO-$d_6$) 2.13 (2H, m, $CO_2CH_2CH_2$), 2.81 (6H, s, $(CH_3)_2$) 3.25 (2H, t, $CH_2N$), 4.42 (2H, t, $CO_2CH_2$), 6.72 (1H, s, 3-H), 7.45 (1H, d, 6-H), 8.01 (1H, d, 8-H), 9.43 (1H, bs, NH) and 12.04 (1H, bs, NH). (Found: C, 41.60; H, 4.34; N, 6.04%. $C_{15}H_{16}Cl_2N_2O_2$. $HBr.0.4H_2O$ requires C, 41.77; H, 4.16; N, 6.49%).

EXAMPLE 36

2-Diisopropylaminoethyl
5,7-dichloro-4-oxo-1,4-dihydroquinoline-2-carboxylate hydrobromide a) Treatment of 4-benzyloxy-5,7-dichloroquinoline-2-carboxylic acid (1 g, Example 33b) with thionyl chloride (10 ml) followed by 2-(diisopropylamino)ethanol (1.63 ml) as described in Example 33c gave 2-diisopropylaminoethyl 4-benzyloxy-5,7-dichloroquinoline-2-carboxylate (0.85 g). δ (360 MHz, DMSO-$d_6$) 0.98 (12H, 2d, $CH_3$), 2.77 (2H, t, $CH_2N$), 3.01 (2H, m, C-H), 4.27 (2H, t, $CO_2CH_2$), 5.49 (2H, s, $OCH_2$), 7.38 (1H, d, p-ArH), 7.44 (2H, t, m-ArH), 7.58 (2H, d, o-ArH), 7.72 (1H, s, 3-H), 7.81 (1H, d, 6-H) and 8.21 (1H, d, 8-H).

b) Treatment of 2-diisopropylaminoethyl 4-benzyloxy-5,7-dichloroquinoline-2-carboxylate (0.85 g) with hydrogen bromide in acetic acid (15 ml, 48%) as described in Example 33d gave 2-diisopropylaminoethyl 5,7-dichloro-4-oxo-1,4-dihydroquinoline-2-carboxylate hydrobromide (0.24 g), m.p. 220° C. (dec). δ (360 MHz, DMSO-$d_6$) 1.33 (12H, 2d, $CH_3$), 3.63 (2H, bs, $CH_2N$), 3.74 (2H, m, CH), 4.63 (2H, t, $CO_2CH_2$), 6.70 (1H, s, 3-H), 7.46 (1H, d, 6-H), 8.02 (1H, d, 8-H), 8.90 (1H, bs, NH) and 12.14 (1H, bs, NH). (Found: C, 45.44; H, 4.87; N, 5.85%. $C_{18}H_{22}Cl_2N_2O_3$. $HBr.H_2O$ requires C, 45.49; H, 5.09; N, 5.90%).

EXAMPLE 37

2-Dimethylamino-1-methylethyl
5,7-dichloro-4-oxo-1,4-dihydroquinoline-2-carboxylate hydrobromide a) Treatment of 4-benzyloxy-5,7-dichloroquinoline-2-carboxylic acid (1.5 g, Example 33b) with thionyl chloride (15 ml) followed by 1-dimethylamino-2-propanol (1.71 ml) as described in Example 33c gave 2-dimethylamino-1-methylethyl 4-benzyloxy-5,7-dichloroquinoline-2-carboxylate (1.47 g). δ (360 MHz, DMSO-$d_6$) 1.34 (3H, d, $CHCH_3$), 2.22 (6H, s, $N(CH_3)_2$), 2.45 and 2.62 (2H, 2dd, $CH_2N$), 5.29 (1H, m, $CO_2CH$), 5.58 (2H, s, $OCH_2$), 7.41 (3H, m, m,p-ArH), 7.59 (2H, d, 0-ArH), 7.69 (1H, s, 3-H), 7.85 (1H, d, 6-H) and 8.12 (1H, d, 8-H).

b) Treatment of 2-dimethylamino-1-methylethyl 4-benzyloxy-5,7-dichloroquinoline-2-carboxylate (1.4 g) with hydrogen bromide in acetic acid (15 ml, 48%) as described in Example 33d gave 2-dimethylamino-1-methylethyl 5,7-dichloroquinoline-2-carboxylate hydrobromide (0.32 g), m.p. 228° C. (dec). δ (360 MHz, DMSO-$d_6$) 1.37 (3H, d, $CHCH_3$), 2.86 (6H, s, $N(CH_3)_2$), 3.59 (2H, m, $CH_2N$), 5.47 (1H, m, $CO_2CH$), 6.81 (1H, s, 3-H), 7.45 (1H, d, 6-H), 8.05 (1H, d, 8-H), 9.45 (1H, bs, NH) and 12.02 (1H, bs, NH). (Found: C, 39.67; H, 3.93; N, 5.94%. $C_{15}H_{16}Cl_2N_2O_3$. 1.4HBr requires C, 39.47; H, 3.84; N, 6.14%).

EXAMPLE 38

2-(4-Morpholinyl)ethyl 5,7-dichloro-4-oxo-1,4-dihydroquinoline-2-carboxylate hydrochloride To a suspension of methyl 5,7-dichloro-4-oxo-1,4-dihydroquinoline-2-carboxylate (1 g) in 4(2-hydroxyethyl)-morpholine (10 ml) at room temperature was added p-toluene sulphonic acid (20 mg), and the reaction mixture was warmed to 80° C. for 3 hours. The cooled mixture was treated with diethylether (50 ml), the resulting precipitate collected and dissolved in methanol (10 ml) and treated with hydrogen chloride in ethylacetate (2 ml of 5M). The mixture was stirred for 30 minutes and the resulting precipitate collected and recrystallised from ethanol-water to give 2-(4-morpholinyl)ethyl 5,7-dichloro-4-oxo-1,4-dihydroquinoline-2-carboxylate hydrochloride (0.45 g), m.p. 233° C. (dec). δ (360 MHz, $D_2O$) 3.35 (4H, bs, morpholinyl-3,5-H), 3.55 (2H, t, $\underline{CH_2}$ N), 4.06 (4H, bs, morpholinyl-2,6-H), 4.85 (2H, t, $CO_2\underline{CH_2}$), 6.73 (1H, s, 3-H), 7.25 (1H, d, 6-H) and 7.40 (1H, d, 8-H). (Found: C, 46.94; H, 4.23; N, 6.84, Cl, 25.92%. $C_{16}H_{16}Cl_2N_2O_4 \cdot HCl \cdot 0.4H_2O$ requires C, 46.73; H, 4.26; N, 6.81; Cl, 25.86%).

EXAMPLE 39

5,7-Dichloro-2-(2-dimethylaminoethyl)carbamoyl-4-oxo-1,4-dihydroquinoline dihydrochloride To N,N-dimethylaminoethanol (5 ml) was added methyl 5,7-dichloro-4-oxo-1,4-dihydroquinoline-2-carboxylate (0.2 g) and the mixture was stirred for 30 minutes at room temperature. Excess N,N-dimethylaminoethanol was removed under reduced pressure and the resulting oil treated with ether (3 ml) to give a pale yellow solid which was filtered, washed with hot ethanol, ether, and then dried. This crude product was treated with hydrogen chloride in ethyl acetate (5 ml of 5M) and methanol (1 ml), then stirred for 30 minutes and the solvent removed under reduced pressure. The product was recrystallised from ethanol-water to yield 5,7-dichloro-2-(2-dimethylaminoethyl)carbamoyl-4-oxo-1,4-dihydroquinoline dihydrochloride (0.24 g), m.p.>280° C. δ (360 MHz, $D_2O$) 3.01 (6H, s, $N(CH_3)_2$), 3.47 (2H, t, $CH_2N$), 3.85 (2H, t, $CONHCH_2$), 6.53 (1H, s, 3-H), 7.18 (1H, d, 6-H) and 7.36 (1H, d, 8-H). (Found: C, 41.87; H, 4.27; H, 10.37%. $C_{14}H_{15}Cl_2N_2O_2 \cdot 2HCl$ requires C, 41.92; H, 4.27; N, 10.37%).

EXAMPLE 40

5,7-Dichloro-2-[2-(4-morpholinyl)ethyl]carbamoyl-4-oxo-1,4-dihydroquinoline hydrochloride To 4-(2-aminoethyl)morpholine (10 ml) was added methyl 5,7-dichloro-4-oxo-1,4-dihydroquinoline-2-carboxylate (1 g) followed by triethylamine (1 ml) and the solution was stirred at room temperature for 16 hours. The reaction mixture was diluted with water (100 ml) and extracted with ethyl acetate (5×50 ml), the combined organic layers were washed with water (2×50 ml), brine (2×50 ml) and dried over magnesium sulphate. The solvent was removed under reduced pressure to yield a crude product (0.4 g). The aqueous layer yielded a further 0.9 g of crude product after standing overnight. The combined crude product was treated with methanol (5 ml) and hydrogen chloride in ethyl acetate (5 ml of 5M), to give a white crystalline product which was recrystallised from ethanol-water to yield 5,7-dichloro-2-[2-(4-morpholinyl)ethyl]carbamoyl-4-oxo-1,4-dihydroquinoline hydrochloride (0.63 g), m.p.>280° C. δ (360 MHz, $D_2O$) 3.48 (6H, $CH_2N$ and morpholinyl-3,5-H), 3.86 (2H, t, $CONH\underline{CH_2}$), 4.00 (4H, bs, morpholinyl-2.6-H), 6.63 (1H, s, 3-H), 7.33 (1H, d, 6-H) and 7.54 (1H, d, 8-H), (Found: C, 46.36: H, 4.57: N, 10.12; Cl, 24.80%. $C_{16}H_{17}Cl_2N_3O_3 \cdot HCl \cdot H_2O$ requires C, 46.23; H, 4.61, N, 10.11; Cl, 25.59%).

EXAMPLE 41

5,7-Dichloro-2-[2-(1-pyrrolidinyl)ethyl]carbamoyl-4-oxo-1,4-dihydroquinoline dihydrochloride Treatment of methyl 5,7-dichloro-4-oxo-1,4-dihydroquinoline-2-carboxylate (2 g) with 1(2-aminoethyl-pyrrolidine (10 ml) as described in Example 39 gave 5,7-dichloro-2-[2-(1-pyrrolidinyl) ethyl]carbamoyl-4-oxo-1,4-dihydroquinoline dihydrochloride (1.5 g)., m.p.>280° C. δ (360 MHz, $D_2O$) 2.02 and 2.16 (4H, 2m, pyrrolidinyl-3,4-H), 3.16 (2H, m, $\underline{CH_2}N$), 3.49 (2H, t, $CONH\underline{CH_2}$), 3.80 (4H, m, pyrrolidinyl-2,5-H), 6.70 (1H, s, 3-H), 7.43 (1H, d, 6-H) and 7.64 (1H, d, 8-H). (Found: C, 45.02; H, 4.52; N, 9.90%. $C_{16}H_{17}Cl_2N_3O_2 \cdot 2HCl$ requires C, 44.99; H, 4.48; N, 9.84%).

EXAMPLE 42

5,7-Dichloro-2-(2-trimethylammonioethyl)carbamoyl-4-oxo-1,4-dihydroquinoline iodide To a suspension of 5,7-dichloro-2-(2-dimethylaminoethyl)carbamoyl-4-oxo-1,4-dihydroquinoline (0.5 g, Example 39) in dry dimethylformamide was added methyl iodide and the mixture was stirred at room temperature for 24 hours. The solvent was removed under reduced pressure to yield the crude product, which was recrystallised from ethanol-water to give 5,7-dichloro-2-(2-trimethylammonioethyl)carbamoyl-4-oxo-1,4-dihydroquinoline iodide (0.39 g), m.p.>280° C. δ (360 MHz, $D_2O$) 3.26 (9H, s, $(CH_3)_3$), 3.62 (2H, t, $\underline{CH_2}N$), 3.94 (2H, t, $CONH\underline{CH_2}$), 6.78 (1H, s, 3-H), 7.50 (1H, d, 6-H) and 7.76 (1H, d, 8-H), (Found: C, 37.06; H, 3.91; N, 8.65; I, 26.14%. $C_{15}H_{18}Cl_2IN_3O_2$ requires C, 36.98; H, 3.91; N, 8.62; I, 26.02%).

EXAMPLE 43

Tablet Preparation

Tablets containing 1.0, 2.0. 25.0. 26.0, 50.0 and 100.0 mg, respectively, of the following compounds are prepared as illustrated below:

5-Bromo-7-methyl-4-oxo-1,4-dihydroquinoline-2-carboxylic acid

2-Diethylaminoethyl 5,7-dichloro-4-oxo-1,4-dihydroquinoline-2-carboxylate 2-(1-Pyrrolindinyl)ethyl 5,7-dichloro-4-oxo-1,4-dihydroquinoline-2-carboxylate 5,7-Dichloro-4-oxo-1,4-dihydroquinoline-2-hydroxamic acid.

| TABLE FOR DOSES CONTAINING FROM 1-25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount-mg | | |
| Active Compound | 26.0 | 50.0 | 100.0 |
| Microcrystalline Cellulose | 52.0 | 100.0 | 200.0 |
| Modified food corn starch | 2.21 | 4.25 | 8.5 |
| Magnesium stearate | 0.39 | 0.75 | 1.5 |

All of the active compound, lactose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.00 mg, 50.0 mg and 100.0 mg of active ingredient per tablet.

What is claimed is:

1. The compound which is 7-chloro-5-iodo-4-oxo-1,4-dihydroquinoline-2-carboxylic acid.

2. A compound of formula II:

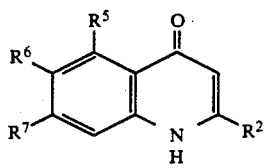

(II)

wherein $R^2$ is a group of formula (iii):

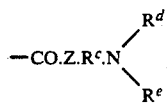

(iii)

in which Z is O or NH; $R^c$ represents $C_{1-6}$ alkylene optionally substituted with a $C_{1-6}$ alkyl group; $R^d$ and $R^e$ independently represent $C_{1-6}$ alkyl, aryl or aryl ($C_{1-6}$)alkyl, or $R^d$ and $R^e$ together with the intervening nitrogen atom represent a pyrrolidino, piperidino or morpholino group; $R^6$ is hydrogen; and $R^5$ and $R^7$ are selected from the group consisting of $C_{1-6}$ alkyl and halogen.

3. A compound according to claim 2 selected from the group consisting of:

2-(diethylamino)ethyl 5,7-dichloro-4-oxo-1,4-dihydroquinoline-2-carboxylate;

5,7-dichloro-2-(2-dimethylaminoethyl)carbamoyl-4-oxo-1,4-dihydroquinoline;

2-(1-pyrrolidinyl)ethyl 5,7-dichloro-4-oxo-1,4-dihydroquinoline-2-carboxylate;

2-(4-morpholinyl)ethyl 5,7-dichloro-4-oxo-1,4-dihydroquinoline-2-carboxylate;

5,7-dichloro-2-[2-(4-morpholinyl)ethyl]carbamoyl-4-oxo-1,4-dihydroquinoline;

5,7-dichloro-2-[2-(1-pyrrolidinyl)ethyl]carbamoyl-4-oxo-1,4-dihydroquinoline;

2-(diisopropylamino)ethyl 5,7-dichloro-4-oxo-1,4-dihydroquinoline-2-carboxylate;

3-(dimethylamino)propyl 5,7-dichloro-4-oxo-1,4-dihydroquinoline-2-carboxylate;

(2-dimethylamino-1-methyl)ethyl 5,7-dichloro-4-oxo-1,4-dihydroquinoline-2-carboxylate;

2-(diethylamino)ethyl 7-chloro-5-iodo-4-1,4-dihydroquinoline-2-carboxylate; and 2-(diethylamino)ethyl 7-bromo-5-ethyl-4-oxo-1,4-dihydroquinoline-2-carboxylate.

4. A pharmaceutical composition comprising an effective amount of a compound according to claim 1 and a pharmaceutically acceptable carrier or excipient.

5. A pharmaceutical composition comprising an effective amount of a compound according to claim 2 and a pharmaceutically acceptable carrier or excipient.

* * * * *